(12) United States Patent
Nishimura et al.

(10) Patent No.: US 7,538,761 B2
(45) Date of Patent: May 26, 2009

(54) INFORMATION PROCESSOR

(75) Inventors: Hirokazu Nishimura, Hachioji (JP);
Hideki Tanaka, Tama (JP); Kenji Yamazaki, Hino (JP)

(73) Assignee: Olympus Corporation, Tokyo (JP)

( * ) Notice: Subject to any disclaimer, the term of this patent is extended or adjusted under 35 U.S.C. 154(b) by 723 days.

(21) Appl. No.: 11/132,039

(22) Filed: May 18, 2005

(65) Prior Publication Data

US 2005/0207645 A1 Sep. 22, 2005

Related U.S. Application Data

(63) Continuation of application No. PCT/JP03/15583, filed on Dec. 5, 2003.

(30) Foreign Application Priority Data

Dec. 12, 2002 (JP) .............. 2002-361326

(51) Int. Cl.
G06F 3/038 (2006.01)
(52) U.S. Cl. .............. 345/204; 382/170; 382/128
(58) Field of Classification Search .............. 345/204; 382/128, 170
See application file for complete search history.

(56) References Cited

U.S. PATENT DOCUMENTS

| | | | |
|---|---|---|---|
| 5,398,685 A * | 3/1995 | Wilk et al. | 600/437 |
| 5,872,861 A * | 2/1999 | Makram-Ebeid | 382/130 |
| 6,059,724 A | 5/2000 | Campell et al. | |
| 2002/0021828 A1 * | 2/2002 | Papier et al. | 382/128 |
| 2002/0131625 A1 * | 9/2002 | Vining et al. | 382/128 |

FOREIGN PATENT DOCUMENTS

| | | |
|---|---|---|
| EP | 1 452 129 A1 | 9/2004 |
| JP | 10-14864 | 1/1998 |
| JP | 2000-311178 | 11/2000 |
| JP | 2001-167203 | 6/2001 |
| JP | 2001-188796 | 7/2001 |
| JP | 2002-109509 | 4/2002 |
| WO | WO 00/60431 | 10/2000 |
| WO | WO 01/69513 A2 | 9/2001 |

OTHER PUBLICATIONS

Benjamin Krevsky, Daniel J. Sher, Brenda J. Horwitz; "Enhanced imaging of angiodysplasias using remote endoscopic digital spectroscopy" Gastrointestinal Endoscopy, Elsevier, NL, vol. 44, No. 5, Nov. 1996, pp. 598-602, XP005127768 ISSN: 0016-5107.*

* cited by examiner

*Primary Examiner*—Bipin Shalwala
*Assistant Examiner*—Kenneth B Lee, Jr.
(74) *Attorney, Agent, or Firm*—Scully, Scott, Murphy & Presser, P.C.

(57) ABSTRACT

According to the invention, a computer includes an information input section, a search criteria input section, an image characteristic value creating section, an image region-of-interest creating section, an information list creating section, a graph executing section and a test executing section. The computer performs processing for inputting information, creating display data and analyzing numeric values in accordance with an event and displays a processing result on a display apparatus. Under this construction, an optimum test procedure can be automatically selected, and work effort can be reduced thereby. Furthermore, by preventing improper selection of a test procedure, an accurate test result can be obtained.

1 Claim, 33 Drawing Sheets

FIG.2

DATABASE (14)

PATIENT INFORMATION TABLE (15)

| PATIENT ID | PATIENT NAME | EXAMINATION DATE | PATIENT SEX | DIAGNOSIS NAME | PATIENT AGES |
|---|---|---|---|---|---|
| 111 | TANAKA | 2000.05.27 | MALE | POLYP | 32 |
| 222 | YAMASAKI | 2000.01.01 | MALE | CANCER | 34 |
| 333 | IMAIZUMI | 2000.04.02 | MALE | NORMAL | 34 |
| 444 | NISHIMURA | 2000.06.05 | MALE | CANCER | 35 |
| : | : | : | : | : | : |

IMAGE INFORMATION TABLE (16)

| IMAGE ID | PATIENT ID | REGISTRATION DATE | PART NAME | IMAGE DATA |
|---|---|---|---|---|
| 1 | 111 | 2000.05.27 | STOMACH | 00010201·· |
| 2 | 222 | 2000.01.01 | STOMACH | 01010100·· |
| 3 | 333 | 2000.04.02 | COLON | F0FFFFF·· |
| 4 | 444 | 2000.06.05 | BRONCHI | 01030301·· |
| : | : | : | : | : |

REGION-OF-INTEREST INFORMATION TABLE (17)

| AREA ID | IMAGE ID | CREATED DATE | AREA DATA | CHARACTERISTIC VALUE 1 | CHARACTERISTIC VALUE 2 |
|---|---|---|---|---|---|
| 1 | 1 | 2000.05.27 | 00000000·· |  | 0.12 |
| 2 | 2 | 2000.01.01 | 11111111·· | 22.5 |  |
| 3 | 4 | 2000.04.02 | 00001111·· | 60.3 | 0.06 |
| 4 | 4 | 2000.06.05 | 00000011·· | 52.3 | 0.07 |
| : | : | : | : | : | : |

FIG.8

INPUT GRAPH CREATION CONDITION /33

METHOD
- HISTOGRAM
- ONE-DIMENSIONAL SCATTER DIAGRAM
- BAR GRAPH (MEAN VALUE)
- TWO-DIMENSIONAL SCATTER DIAGRAM

FIRST DATA VALUE
- PATIENT AGE
- FIRST CHARACTERISTIC VALUE
- SECOND CHARACTERISTIC VALUE

CATEGORY
- DIAGNOSIS NAME
- PART NAME
- PATIENT SEX

SECOND DATA VALUE
- PATIENT AGE
- FIRST CHARACTERISTIC VALUE
- SECOND CHARACTERISTIC VALUE

34 — EXECUTE | CANCEL

FIG.9

INPUT TEST EXECUTION CONDITION /35

CATEGORY
- DIAGNOSIS NAME
- PART NAME
- PATIENT SEX

DATA VALUE
- PATIENT AGE
- FIRST CHARACTERISTIC VALUE
- SECOND CHARACTERISTIC VALUE

36 — EXECUTE | CANCEL

FIG.11

DISPLAY COLUMN MANAGEMENT TABLE /41

| DISPLAY NO. | DISPLAY TEXT | EDIT ATTRIBUTE | LEVEL | DISPLAY ATTRIBUTE |
|---|---|---|---|---|
| 1 | IMAGE ID | 3 | IMAGE | TEXT |
| 2 | PATIENT ID | 3 | PATIENT | TEXT |
| 3 | PATIENT NAME | 3 | PATIENT | TEXT |
| 4 | EXAMINATION DATE | 2 | PATIENT | DATE |
| 5 | PART NAME | 1 | IMAGE | TEXT |
| 6 | DIAGNOSIS NAME | 1 | IMAGE | TEXT |
| 7 | FIRST CHARACTERISTIC VALUE | 3 | REGION OF INTEREST | NUMERICAL VALUE |
| 8 | SECOND CHARACTERISTIC VALUE | 3 | REGION OF INTEREST | NUMERICAL VALUE |
| 9 | PATIENT AGE | 3 | PATIENT | NUMERICAL VALUE |

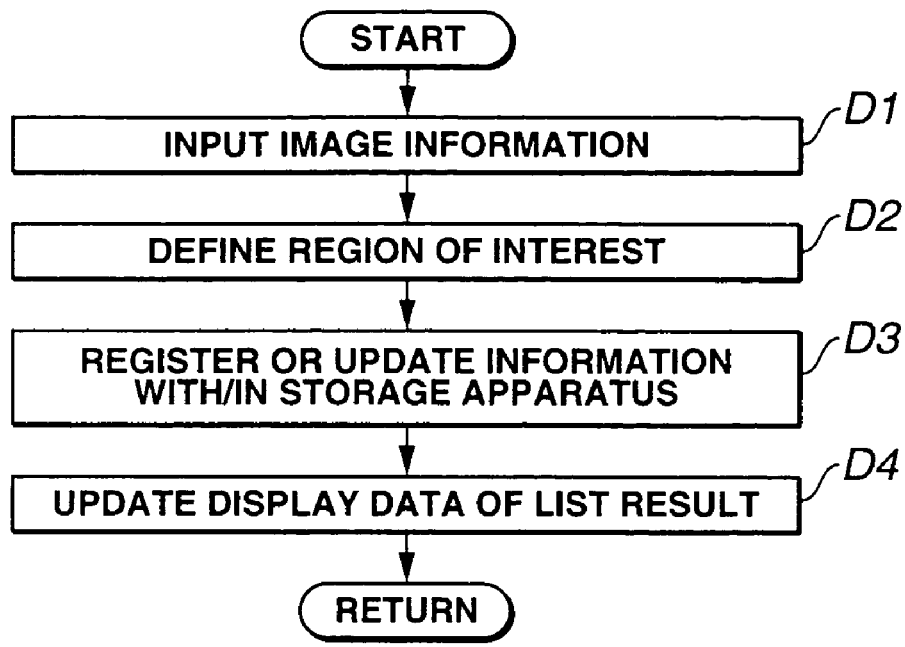
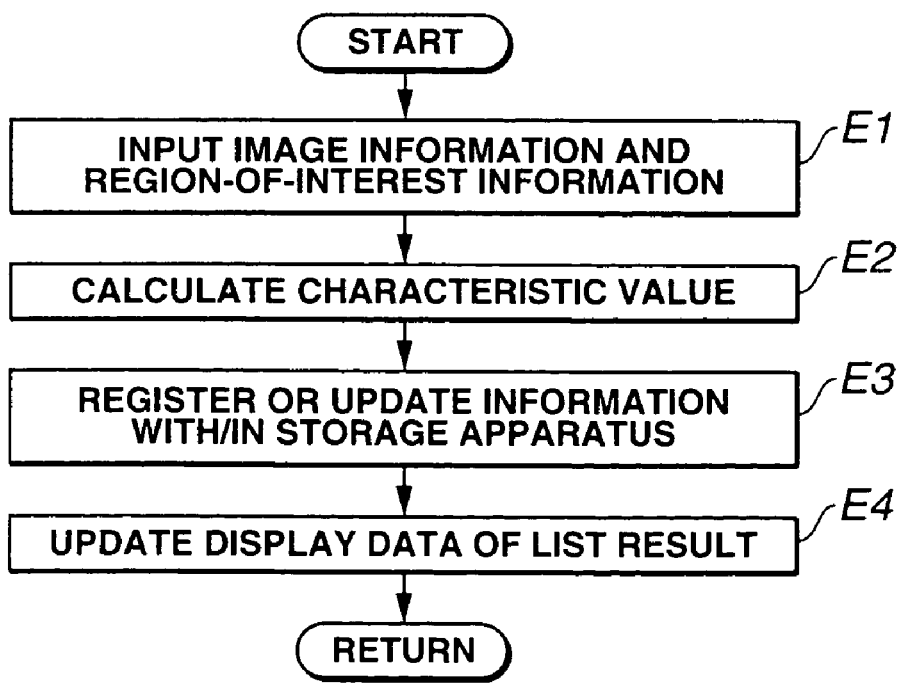

FIG.20

| TEST GROUP : | [PATIENT SEX]   MALE   FEMALE |
|---|---|
| USED CHARACTERISTIC VALUE : | AGE UPON EXAMINATION |
| PATIENT SEX     N | AGE UPON EXAMINATION (MEAN VALUE ± STANDARD DEVIATION MINIMUM VALUE/MAXIMUM VALUE) |

MALE              13          26.000±3.000         23.000/32.000
FEMALE         27          51.429±6.027         24.000/76.000

TEST OF 2 GROUPS WILL BE EXECUTED.
NOT HOMOSCEDASTIC.

TEST PROCEDURE OF MEAN VALUES         WELCH'S t-TEST
OF APPLIED TWO GROUP :                         (BOTH SIDE TEST)

$P<0.05$ FROM $|T| = 2.622 > 18(0.025) = 2.306$

DISPLAY COLUMN MANAGEMENT TABLE (41)

| DISPLAY NO. | DISPLAY TEXT | EDIT ATTRIBUTE | LEVEL | DISPLAY ATTRIBUTE |
|---|---|---|---|---|
| 1 | IMAGE ID | 3 | IMAGE | TEXT |
| 2 | PATIENT ID | 3 | PATIENT | TEXT |
| 3 | PATIENT NAME | 3 | PATIENT | TEXT |
| 4 | EXAMINATION DATE | 2 | PATIENT | DATE |
| 5 | PART NAME | 1 | IMAGE | TEXT |
| 6 | PART NAME | 1 | REGION OF INTEREST | TEXT |
| 7 | USED DRUG | 3 | PATIENT | NUMERICAL VALUE |
| 8 | | | | |
| 9 | | | | |

FIG.23

CHANGE SETTING OF GRAPH DISPLAY — 45

| MARKER | FORM | COLOR | SIZE | DISPLAY ORDER |
|---|---|---|---|---|
| CANCER | ○ ▷ | RED ▷ | 3 ▷ | 1 ▷ |
| ADENOMA | × ▷ | BLUE ▷ | 3 ▷ | 2 ▷ |

TEXT DISPLAY FORM

| | FONT | SIZE |
|---|---|---|
| TITLE | MINCHO ▷ | 12 POINT ▷ |
| LEGEND | GOTHIC ▷ | 10 POINT ▷ |
| X-AXIS | GOTHIC ▷ | 10 POINT ▷ |
| Y-AXIS | GOTHIC ▷ | 10 POINT ▷ |

☐ REFLECT CHANGE TO OTHER GRAPHS

EXECUTE — 46

CANCEL

FIG.24

| CHANGE SETTING OF GRAPH DISPLAY (GRAPH A) | | | | |47|
|---|---|---|---|---|
| CATEGORY CLASS NAME | FORM | SIZE | COLOR (R, G, B) | DISPLAY ORDER |
| CANCER | ○ | 3 | (255,0,0) | 1 |
| ADENOMA | × | 3 | (0,0,255) | 2 |
| | | | | |
| TEXT DISPLAY POSITION | FONT | SIZE | | |
| TITLE | MINCHO | 12 POINT | | |
| LEGEND | GOTHIC | 10 POINT | | |
| X-AXIS | GOTHIC | 10 POINT | | |
| Y-AXIS | GOTHIC | 10 POINT | | |

FIG.25

| MARKER SETTING TABLE (DIAGNOSIS NAME) | | | | |48|
|---|---|---|---|---|
| CATEGORY CLASS NAME | FORM | SIZE | COLOR (R, G, B) | DISPLAY ORDER |
| NORMAL | ○ | 3 | (255,0,0) | 1 |
| CANCER | × | 3 | (0,0,255) | 2 |
| ADENOMA | △ | 3 | (0,255,0) | 3 |
| POLYP | ◎ | 3 | (255,0,255) | 4 |
| ULCER | □ | 3 | (0,255,255) | 5 |

SCATTER DIAGRAM OF
FIRST CHARACTERISTIC VALUE AND
SECOND CHARACTERISTIC VALUE

○ : NORMAL
× : CANCER

FIG.28

INPUT GRAPH CREATION CONDITION /33

METHOD:
- HISTOGRAM
- ONE-DIMENSIONAL SCATTER DIAGRAM
- BAR GRAPH (MEAN VALUE)
- TWO-DIMENSIONAL SCATTER DIAGRAM

FIRST DATA VALUE:
- PATIENT AGE
- FIRST CHARACTERISTIC VALUE
- SECOND CHARACTERISTIC VALUE

CATEGORY:
- DIAGNOSIS NAME
- PART NAME
- PATIENT SEX

SECOND DATA VALUE:
- PATIENT AGE
- FIRST CHARACTERISTIC VALUE
- SECOND CHARACTERISTIC VALUE

- ⦿ LAST SETTING RELATING TO GRAPH CREATION —50
- ○ LAST SETTING RELATING TO GRAPH TYPE —51
- ○ LAST SETTING RELATING TO TEST —52

34 — [ EXECUTE ]　[ CANCEL ]

FIG.29

INPUT TEST EXECUTION CONDITION /35

CATEGORY: DIAGNOSIS NAME, PART NAME, PATIENT SEX

DATA VALUE: PATIENT AGE, FIRST CHARACTERISTIC VALUE, SECOND CHARACTERISTIC VALUE

○ LAST SETTING RELATING TO TEST —55
◉ LAST SETTING RELATING TO GRAPH CREATION —56

36 — [EXECUTE] [CANCEL]

FIG.30

SETTING HISTORY TABLE /58

| TYPE | PROCEDURE | CATEGORY | FIRST DATA VALUE | SECOND DATA VALUE |
|---|---|---|---|---|
| TEST | MEAN VALUE TEST | DIAGNOSIS NAME | PATIENT AGE | |
| GRAPH | ONE-DIMENSIONAL SCATTER DIAGRAM | PATIENT SEX | FIRST CHARACTERISTIC VALUE | |
| HISTOGRAM | | PATIENT SEX | SECOND CHARACTERISTIC VALUE | |
| ONE-DIMENSIONAL SCATTER DIAGRAM | | PATIENT SEX | FIRST CHARACTERISTIC VALUE | |
| TWO-DIMENSIONAL SCATTER DIAGRAM | | PART NAME | FIRST CHARACTERISTIC VALUE | SECOND CHARACTERISTIC VALUE |
| BAR GRAPH (MEAN VALUE) | | DIAGNOSIS NAME | FIRST CHARACTERISTIC VALUE | |
| | | | | |
| | | | | |
| | | | | |

| IMAGE INFORMATION TABLE | | | | | |
|---|---|---|---|---|---|
| IMAGE ID | PATIENT ID | REGISTRATION DATE | PART NAME | IMAGE DATA | IMPORTANCE |
| 1 | 111 | 2000.05.27 | STOMACH | 00010201·· | 1 |
| 2 | 222 | 2000.01.01 | STOMACH | 01010100·· | 0 |
| 3 | 333 | 2000.04.02 | COLON | F0FFFFF·· | 0 |
| 4 | 444 | 2000.06.05 | BRONCHI | 01030301·· | 1 |
| : | : | : | : | : | : |

FIG.42

| IMAGE ID | PATIENT ID | PATIENT NAME | EXAMINATION DATE | PART NAME | DIAGNOSIS NAME | CHARACTERISTIC VALUE 1 | CHARACTERISTIC VALUE 2 | RIGHT-WRONG JUDGMENT | DIAGNOSIS NAME BASED ON IDENTIFICATION |
|---|---|---|---|---|---|---|---|---|---|
| 1 | 111 | TANAKA | 2000.05.27 | STOMACH | NORMAL | 26.1 | 0.12 | × | NORMAL |
| 2 | 222 | YAMASAKI | 2000.01.01 | STOMACH | NORMAL | 22.5 | 0.10 | ○(-) | NORMAL |
| 3 | 333 | IMAIZUMI | 2000.04.02 | COLON | NORMAL | 31.8 | 0.05 | ○ | NORMAL |
| 4 | 444 | NISHIMURA | 2000.06.05 | BRONCHI | CANCER | 60.3 | 0.06 | ×(-) | NORMAL |
| 4 | 444 | NISHIMURA | 2000.06.05 | BRONCHI | CANCER | 52.3 | 0.07 | ○ | CANCER |
| .. | .. | .. | .. | .. | .. | .. | .. | .. | .. | ental apparatus.
INFORMATION PROCESSOR

CROSS REFERENCE TO RELATED APPLICATION

This application is a continuation application of PCT/JP03/15583 filed on Dec. 5, 2003 and claims the benefit of Japanese Application No. 2002-361326 filed in Japan on Dec. 12, 2002, the entire contents of each of which are incorporated herein by their reference.

BACKGROUND OF THE INVENTION

1. Field of the Invention

The present invention relates to an information processor for creating statistical information from processing data.

2. Description of the Related Art

In the medical field, diagnoses have been widely performed by using image pickup equipment such as an X-ray, CT, MRI, ultrasonic observation apparatus and an endoscope apparatus.

For example, in an endoscope apparatus, a long and narrow insert portion thereof is inserted into a body cavity so that an organ in the body cavity can be observed and diagnosed with reference to a monitor screen by using an image pickup unit such as a solid-state image pickup device. Furthermore, an ultrasonic endoscope apparatus has been also widely used by which ultrasound is irradiated to the organ in the body cavity so that a state of the organ in the body cavity can be observed, examined or diagnosed with reference to a monitor screen based on reflection or transmittance, for example, of the ultrasound.

An image filing system has been also widely used by which various kinds of information can be added to an image picked up by these apparatus and the image with the information can be stored so as to search, retrieve and display as required.

However, the final diagnosis using these medical image pickup apparatus largely depends on the subjectivity of a doctor. Therefore, the supply of diagnosis support information directly connecting to an objective and numeric diagnosis has been demanded.

The diagnosis support information may include conversion of image observation into numbers, display of statistical information relating to a disease and display of a type of disease based on an identification and categorization result using an amount of feature.

Japanese Unexamined Patent Application Publication No. 10-14864, for example, discloses an information processor supplying diagnosis support information. This provides diagnosis support information based on many patients, examinations and image information recorded in an image filing system.

SUMMARY OF THE INVENTION

An information processor according to the invention includes a storage unit for storing processing target data to be processed, a statistical processing unit for determining a statistical processing technique by performing statistical processing on the processing target data in accordance with a characteristic of the processing target data and for creating statistical information by processing the processing target data by the determined statistical processing technique and a display control portion for causing a display unit to display statistical information created by the statistical processing unit.

The other features and advantages of the invention will be sufficiently apparent from the following descriptions.

BRIEF DESCRIPTION OF THE DRAWINGS

FIGS. 1 to 21 relate to a first embodiment of the invention;

FIG. 1 is a configuration diagram showing a configuration of an information processing;

FIG. 2 is a diagram showing a construction of a database stored in a storage device in FIG. 1;

FIG. 3 is a configuration diagram showing a configuration of an information input section in FIG. 1;

FIG. 4 is a diagram showing an information update window displayed by a display apparatus under the control of the information input section in FIG. 1;

FIG. 5 is an information update window displayed by the display apparatus under the control of the information input section in FIG. 1;

FIG. 6 is a search criteria input window displayed by the display apparatus under the control of an image characteristic value creating section in FIG. 1;

FIG. 7 is a configuration diagram showing a configuration of the image characteristic value creating section in FIG. 1;

FIG. 8 is a diagram showing a graph creation condition input window displayed by the display apparatus under the control of a graph executing section in FIG. 1;

FIG. 9 is a diagram showing a test execution condition input window displayed by the display apparatus under the control of a test executing section in FIG. 1;

FIG. 10 is a diagram showing a list table created by an information list creating section in FIG. 1;

FIG. 11 is a diagram showing a display column management table managing the information list in FIG. 10;

FIG. 12 is a flowchart showing a flow of event loop processing by a computer in FIG. 1;

FIG. 13 is a flowchart showing a flow of first processing branching off from the processing in FIG. 12;

FIG. 14 is a flowchart showing a flow of second processing branching off from the processing in FIG. 12;

FIG. 15 is a flowchart showing a flow of third processing branching off from the processing in FIG. 12;

FIG. 16 is a flowchart showing a flow of fourth processing branching off from the processing in FIG. 12;

FIG. 17 is a flowchart showing a flow of fifth processing branching off from the processing in FIG. 12;

FIG. 18 is a flowchart showing a flow of sixth processing branching off from the processing in FIG. 12;

FIG. 19 is a flowchart showing a flow of a test procedure to be executed by a test executing section in FIG. 1;

FIG. 20 is a diagram showing a test result displayed by the display apparatus under the control of the test executing section in FIG. 1; and FIG. 21 is a diagram showing a display column management table stored in a storage device according to a variation example of the first embodiment.

FIGS. 22 to 27 relate to a second embodiment of the invention;

FIG. 22 is a block diagram showing a configuration of a graph executing section;

FIG. 23 is a diagram showing a graph display setting change window on which change processing is performed by a display attribute changing section in FIG. 22;

FIG. 24 is a diagram showing a graph display setting table managed by a graph window managing section in FIG. 22;

FIG. 25 is a diagram showing a marker setting table managed by the graph window managing section in FIG. 22;

FIG. 26 is a diagram showing a display example in a two-dimensional scatter diagram created by the graph executing section in FIG. 22; and FIG. 27 is a flowchart illustrating processing for changing display data of a graph created by the graph executing portion in FIG. 22.

FIGS. 28 to 31 relate to a third embodiment of the invention;

FIG. 28 is a diagram showing a graph creation condition input window displayed by the display apparatus under the control of the graph executing section;

FIG. 29 is a diagram showing a test execution condition input window displayed by the display apparatus under the control by the test executing section;

FIG. 30 is a diagram showing a setting history table held in the storage apparatus; and FIG. 31 is a flowchart illustrating a flow of processing by the graph executing section and test executing section.

FIG. 32 is a diagram showing an image select switch provided in an endoscopic observation apparatus;

FIG. 33 is a diagram showing an image information table; and

FIG. 34 is a flowchart showing a processing flow of second processing branching off from the processing in FIG. 12.

FIG. 35 is a configuration diagram showing a configuration of an information processor;

FIG. 36 is a diagram showing a list table created by an information list creating section in FIG. 35; and FIG. 37 is a flowchart showing processing flow of second processing branching off from the processing in FIG. 12.

FIG. 38 is a configuration diagram showing a configuration of an information processor; and FIG. 39 is a flowchart showing a processing flow by a download section in FIG. 38.

FIGS. 40 to 44 relate to a seventh embodiment of the invention;

FIG. 40 is a configuration diagram showing a configuration of an information processor;

FIG. 41 is a diagram showing a display example in a two-dimensional scatter diagram created by a graph executing section in FIG. 40;

FIG. 42 is a diagram showing a list table created by an information list creating section in FIG. 40;

FIG. 43 is a flowchart showing a processing flow of an identification and categorization executing section in FIG. 40; and FIG. 44 is a flowchart showing a processing flow by an identification and categorization executing section in a variation example of the seventh embodiment.

FIG. 45 is a block diagram showing a configuration of a graph executing section;

FIG. 46 is a diagram showing a display window displayed on a display apparatus under the control of a related information creating section in FIG. 45; and FIG. 47 is a flowchart showing a processing flow by a graph window data managing section in FIG. 45.

DESCRIPTION OF THE PREFERRED EMBODIMENTS

Figure 1:
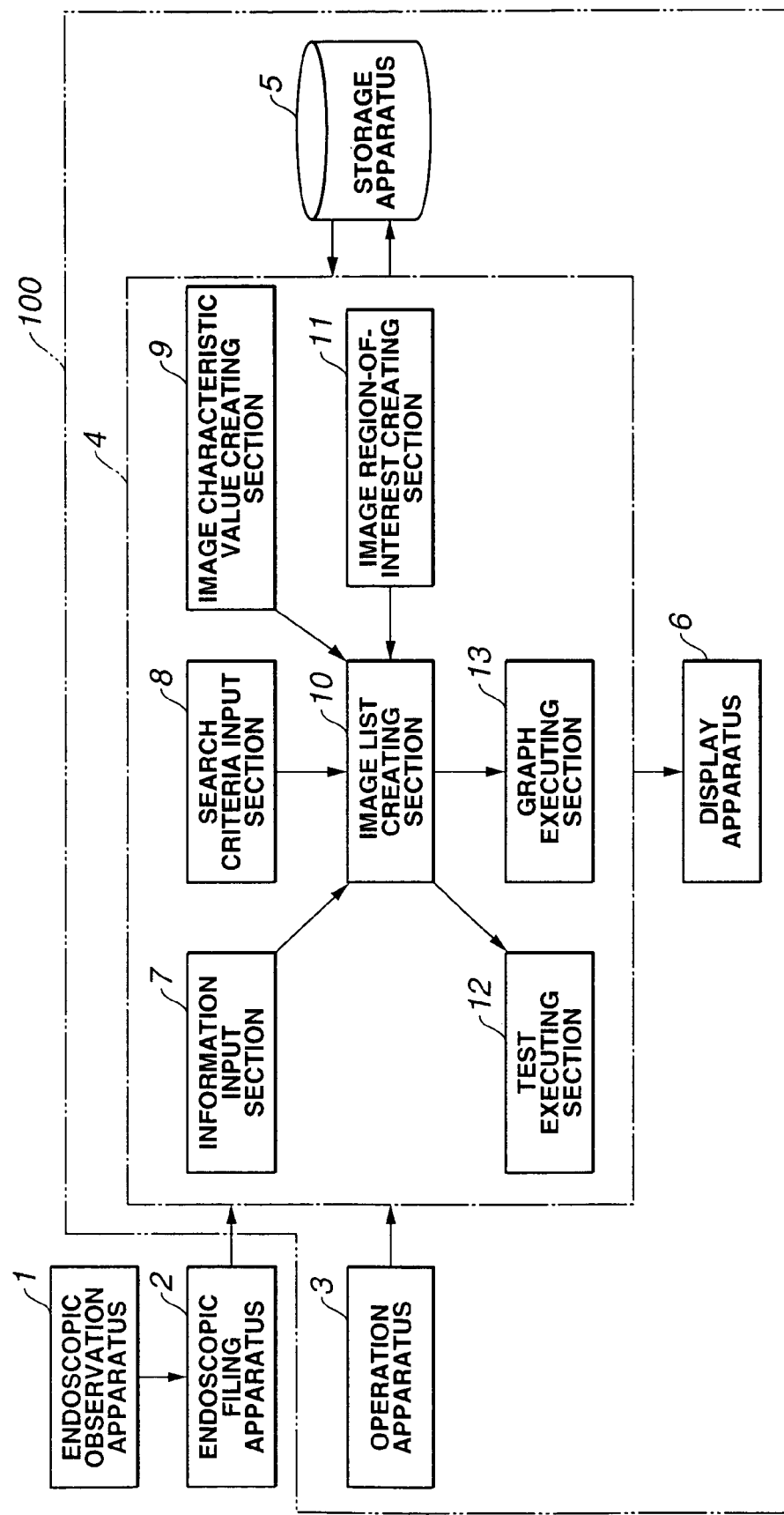

The invention will be described in detail with reference to attached drawings.

First of all, before describing embodiments, details of diagnosis support information provided by an information processor of the invention will be described.

Medical diagnoses are generally made subjectively based on determination by doctors. This means that diagnosis results may differ due to differences in experience and/or subjective determination by doctors.

In order to solve the problems, it is an object of an information processor of the invention to make accurate diagnoses having no variations by providing quantified objective information as diagnosis support information through objective display of information for image observation, and display of a disease categorization result by an identification and categorization technique such as a linear discriminant function and a neural network.

Diagnosis support information may include Variations [1] to [3] below. These kinds of diagnosis support information are created adaptively in accordance with an image pickup equipment (modality which will be described by using an endoscope system, for example, according to the invention), an examined part, a focused disease and so on.

Variation [1]: Conversion of Image Observation to Number

A tone may be used as one of important image observations in the medical endoscope field. An IHb is widely used as a numeric value (characteristic value) objectively representing a difference in tone.

For each of pixels of an endoscopic image including RGB color signals, an IHb is a value calculated by:

$$32\log_2 R_i/G_i$$

An IHb is known as a value correlated to an amount of submucosal blood. As the level of red increases in the tone of a mucous membrane, the IHb value increases. Here, i is a numerical subscript indicating a number of a pixel, and a mean value in an entire image or defined range is used as diagnosis support information.

Analysis of a form of blood vessels may be also used as one of important image observation in the medical endoscope field. In this case, a form of blood vessels (including a proportion of blood vessels in an image (blood-vessel-to-area ratio), a thickness of a blood vessel, a length of a blood vessel, the numbers of branches and intersections of blood vessels, and unclearness of blood vessels) is converted to numbers to numerically evaluate the form of blood vessels, which has been determined subjectively before.

For example, a ratio of blood vessels to an area can be calculated as a proportion of blood vessels in a defined area by binarizing G signals of RGB color signals with respect to a threshold value determined adaptively to an image and separating a mucous membrane and the blood vessels.

Based on these characteristic values of the observations, a doctor makes a final diagnosis. Thus, an observation generally depending on a subjective determination such as "the surface of the mucous membrane is red" and "a proportion of the blood vessels is large" can be provided as an objective and numerical observation with reference to diagnosis support contents according to an embodiment, which will be described below. As a result, the objective and numerical observation can be shared among doctors as universal observation evaluation and diagnosis information.

Variation [2]: Display of Statistical Information Relating to Disease

A relationship between a characteristic value and a diagnosis can be clarified by collecting multiple characteristic values described in Variation [1] for each diagnosis made by a doctor and applying statistical processing. Thus, a new diagnosis standard can be found.

For example, if a normal group and a disease group have a significant difference therebetween as a result of collection of IHbs for the normal group and the disease group and test of differences of mean values of the IHbs, the IHbs can be a standard for diagnosing a normal state and a disease.

Therefore, the validity for the use of applicable observations and the characteristic values as the determination standard for disease diagnoses can be objectively determined.

By using mean values and standard errors of characteristic values of groups, a new diagnosis method can be developed for determining a possibility of a disease based on values of characteristic values.

Variation [3]: Display of Disease Type Based On Result of Identification and Categorization Using Characteristic Values A multivariable analysis including an identification and categorization method such as a linear discriminant function and a neural network may be performed by collecting multiple characteristic values described in Variation [1] for each diagnosis to be made by a doctor. Thus, a new diagnosis standard can be found in which a possibility of a disease can be determined from the characteristic values.

For example, a normal group and a disease group can be discriminated as a result of collection of characteristic values such as a ratio of blood vessels to an area and IHbs for the normal group and the disease group and implementation of multivariable analysis. In other words, the discrimination method using characteristic values can be highly possibly a diagnosis technique for discriminating a normal state and a disease.

Therefore, a discovery supporting system can be developed whereby diagnosis support contents according to any one of embodiments are applied in realtime in a screening work in which a doctor subjectively determines and discovers a disease part intensively with reference to an image so that a position highly possibly having a disease can be pointed and missing the position can be prevented.

The information processing using characteristic values, statistical information and identification and categorization results as described above can be performed as required on various observations involving modality, components and/or shade information of not only endoscopic images but also X-ray and ultrasonic images. Furthermore, similar diagnosis support information can be provided as numeric values other than characteristic values obtained from images such as the number of red blood cells from a blood examination.

Embodiments

Embodiments of the invention will be described below with reference to drawings.

First Embodiment (Construction)

As shown in FIG. 1, an information processor 100 according to a first embodiment includes a computer 4, an operation apparatus 3, a storage apparatus 5, and a display apparatus 6. An endoscopic observation apparatus 1 and an endoscopic filing apparatus 2 are connected to the computer 4. The endoscopic observation apparatus 1 images an internal part of a living body and outputs analog image signals. The endoscopic filing apparatus 2 creates image data from analog image signals output by the endoscopic observation apparatus 1. The computer 4 performs different kinds of data processing. The operation apparatus 3 includes a keyboard and/or a mouse. The storage apparatus 5 includes a hard disk. The display apparatus 6 includes a CRT monitor, a liquid crystal monitor, a plasma monitor or the like.

The computer 4 repeatedly performs an event loop and performs processing in accordance with an occurring event.

The computer 4 includes an information input section 7, a search criteria input section 8, an image characteristic value creating section 9, an image region-of-interest creating section 11, an information list creating section 10, a graph executing section 13 and a test executing portion 12. In accordance with an event, the computer 4 performs input of information, creation of display contents and implementation of numerical analysis processing and displays a processing result on the display apparatus 6.

Figure 12:
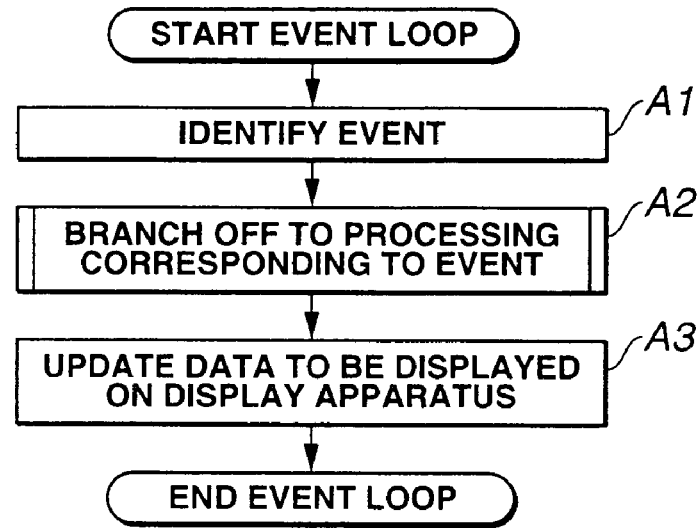

The storage apparatus 5 is connected to the computer 4 and includes a database 14 shown in FIG. 12. The database 14 is an SQL database and includes a patient information table 15, an image information table 16, and a region-of-interest information table 17. Patient information, image information and region-of-interest information are recorded in the database 14.

The patient information table 15 stores patient information such as patient IDs and patient names. A record in the patient information table 15 can be uniquely identified by a patient ID.

The image information table 16 stores image information such as image data and image IDs. A record in the image information table 16 can be uniquely identified by an image ID.

The region-of-interest information table 17 stores region-of-interest information such as area IDs, area data and characteristic values. A record in the area information table 17 can be uniquely identified by an area ID.

Here, a region of interest is a rectangular area or an area surrounded by a free contour, which is defined within an image, and is an area including an interesting target such as a lesion. A characteristic value is an indicator value for evaluating a disease quantitatively such as an IHb, which is described above, and a ratio of blood vessels to an area.

Each code in the region-of-interest information table 17 is linked to a corresponding record in the image information table 16 by an image ID. Each record in the image information table 16 is linked to a corresponding record in the patient information table 15 by a patient ID. Thus, information recorded in the database 14 is managed under a hierarchical structure having patient information, image information and region-of-interest information.

The operation apparatus 3 is used to select a menu item, instruct through buttons and input strings in accordance with data displayed on the display apparatus 6.

An event is caused within the computer 4 in response to a selection of a menu item and/or pressing of a button through a manipulation on the operation apparatus 3.

Figure 3:
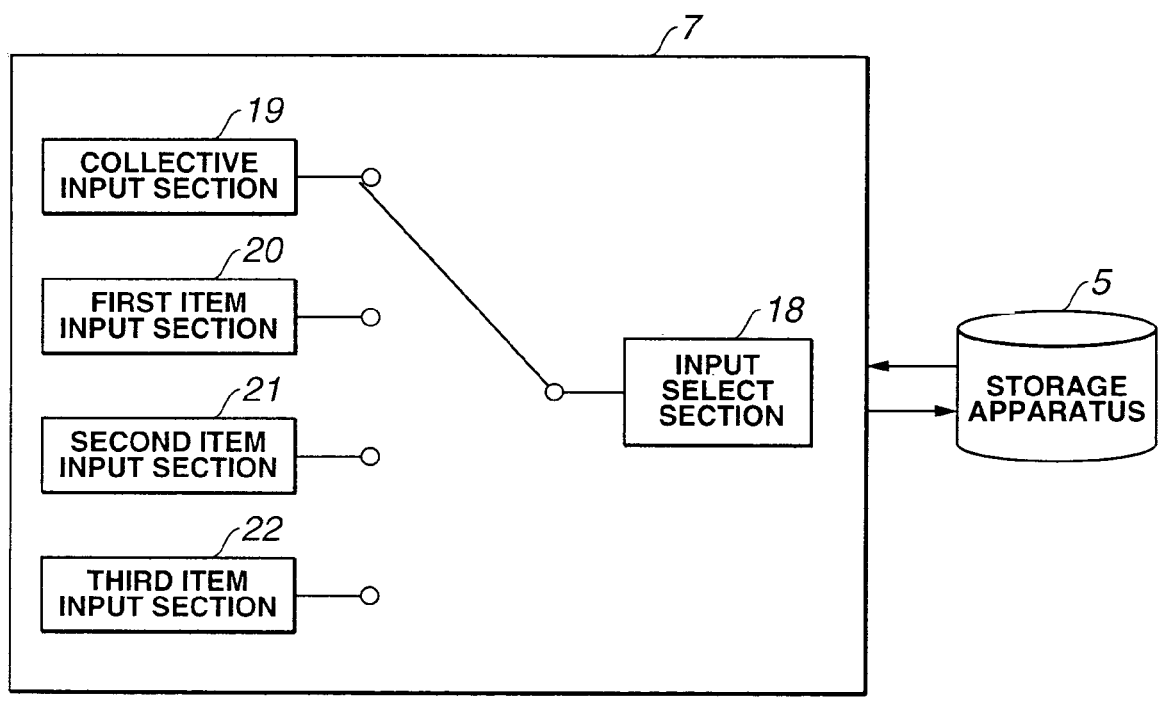
Figures 4, 5:
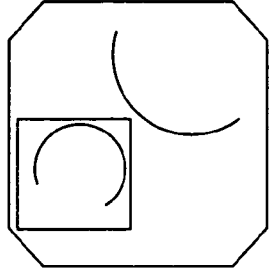

As shown in FIG. 3, the information input section 7 includes an input selecting section 18, a collective input section 19, a first item input section 20, a second item input section 21 and a third item input section 22. The information input section 7 causes the display apparatus 6 to display input windows, which are shown in FIG. 4 and the upper, medium and lower parts in FIG. 5. The data are updated by editing information stored in the patient information table 15 and the image information table 16.

Furthermore, processing is performed for newly recording image information, such as image data output by the endoscopic filing apparatus 2, in the image information table 16.

Figures 6, 7:
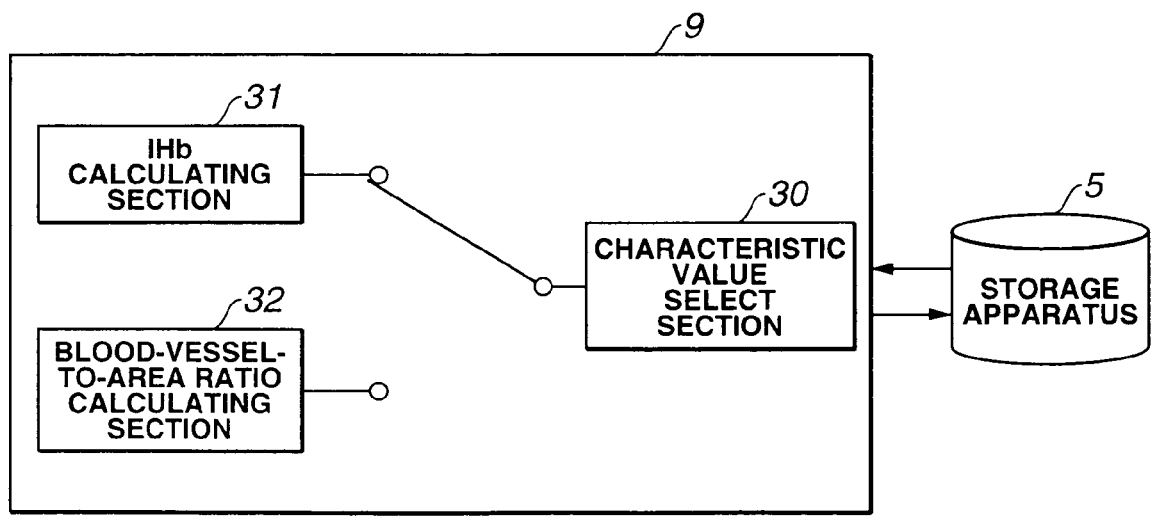

The search criteria input section 8 causes the display apparatus 6 to display a search criteria input window 28 in FIG. 6. The database 14 is searched based on a search criterion such as a patient name, examination date and diagnosis name input by a user. The patient information, image information and region-of-interest information as a result of the search are held in the computer 4.

As shown in FIG. 7, the image characteristic value creating section 9 includes a characteristic value selecting section 30, an IHb calculating section 31, and a blood-vessel-to-area ratio calculating section 32. The image characteristic value creating section 9 creates a characteristic value calculated from image data of the internal part of a region of interest based on image information and region-of-interest information held in the computer 4.

The IHb calculating portion 31 calculates a characteristic value [IHb] described above from image data. The blood-vessel-to-area ratio calculating section 32 calculates the characteristic value [ratio of blood vessels to an area] from image data.

The image region-of-interest creating section 11 defines a region of interest within an image selected by a user through the operation apparatus 3.

The graph executing section 13 creates a graph such as a histogram, a one-dimensional scatter diagram, a two-dimensional scatter diagram and a bar graph under a condition selected on the graph creation condition input window 33 shown in FIG. 8 and based on patient information, image information and region-of-interest information held in the computer 4 and displays the graph on the display apparatus 6.

The test executing section 12 executes a test of a difference between mean values under a condition specified on the test execution condition input window 35 shown in FIG. 9 and based on patient information, image information and region-of-interest information held in the computer 4.

Figure 10:
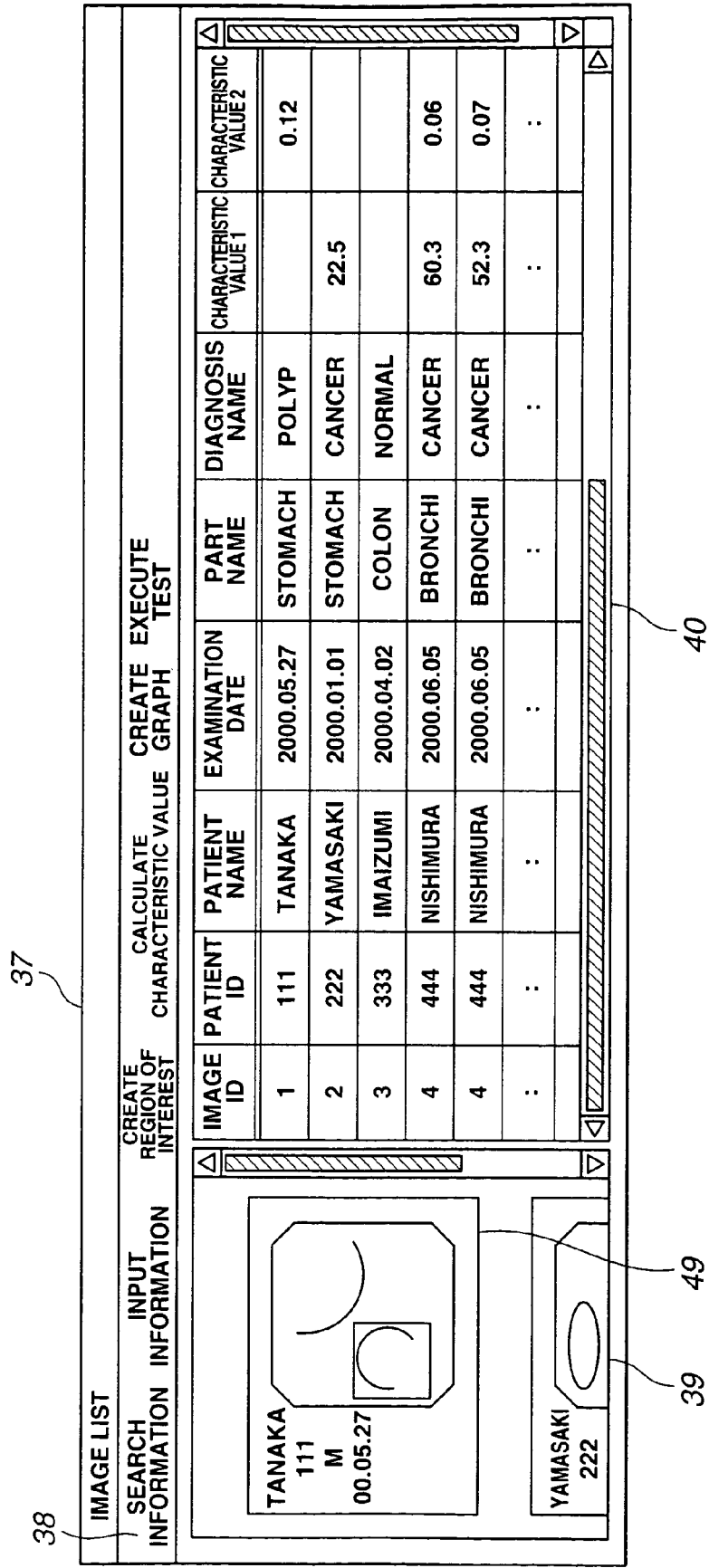

The information list creating section 10 creates the list table 37 shown in FIG. 10 based on patient information, image information and region-of-interest information held in the computer 4. The list table 37 includes a reduced image list 39 and an information list 40.

The list table 37 has a menu 38, and an event subject to various kinds of processing is caused in response to selection of an item under the menu 38.

A reduced image 49 is an image reduced based on image data in the image information table. When area information relating to image information is provided, data resulting from a synthesis of area data within region-of-interest information and image data is reduced so that a reduced image having an area on an image can be created and be used.

The information list 40 is a viewable list having patient information, image information and region-of-interest information. On the information list 40, display text and a display order of column items of the information list 40 are determined based on a display column management table 41 stored in the storage apparatus 5.

An example of the display column management table 41 is shown in FIG. 11. The display column management table 41 holds edit attributes, a hierarchy of display information, and display attributes connected to each other as well as a order of displaying column items and display text on the information list 40.

(Operation)

The computer 4 repeatedly performs an event loop based on a flow diagram in FIG. 12 and performs, in branch processing thereof, information search, display of a list of search results, registration or editing of information, definition of a region of interest into an image, calculation of a characteristic value within a region of interest, display of information in a graph form and test of information.

At a step A1 in FIG. 12, an event occurring in the computer 4 is obtained in response to a manipulation on an operation apparatus such as selection of a menu item, and a type of the event is identified. At a step A2, branching from the processing in accordance with the discriminated type of the event, processing in accordance with the type of the event is performed. At a step A3, display contents on the display apparatus 6 are updated based on the processing result. At the step A2, the branching processing flow is shown in FIGS. 13 to 18.

Figure 13:
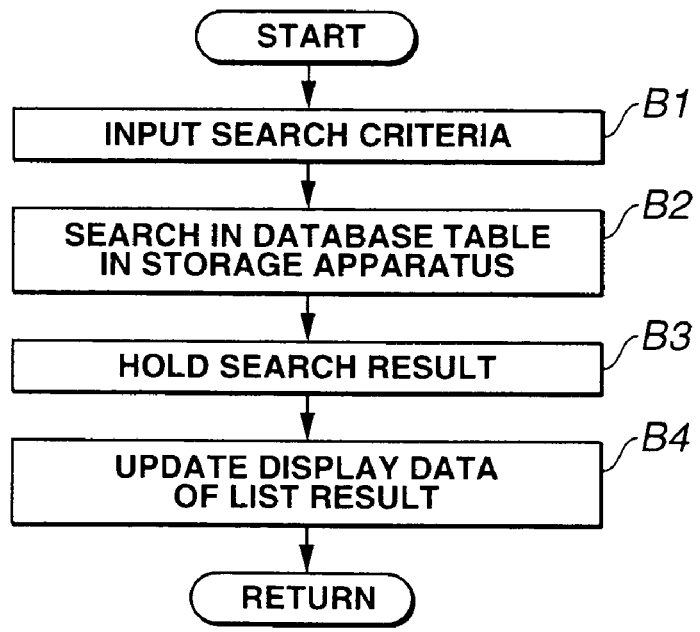

FIG. 13 is a flow diagram illustrating processing of searching diagnosis support information and displaying a list of the search results.

At a step B1, the search criteria input section displays the search criteria input window 28 shown in FIG. 6. A user may input a patient name and/or an examination date and/or a diagnosis name through the operation apparatus 3 and press a search button 29 within the search criteria input window 28. In response thereto, input strings are created as a search key for the database 14.

At a step B2, the search criteria input section 8 connects the patient information table 15 and the image information table 16 based on the created search key to the database 14 and retrieves patient information and image information matching with the search key. Furthermore, the search criteria input section 8 searches the region-of-interest information table 17 by using an image ID of the retrieved image information as a search key, retrieves region-of-interest information matching with the search key and creates an information set including patient information, image information and region-of-interest information.

At a step B3, the search criteria input section 8 causes the information set searched and retrieved at the step B2 to be held in the computer 4.

At a step B4, the information list creating section 10 repeatedly displays on the list table 37 a pair of a reduced image and an information list at one row for each of the sets including patient information, image information and region-of-interest information held in the computer 4. For creating and displaying the list table 37, the information list creating section 10 uses the display column management table 41 stored in the storage apparatus 5. During creation of a column, display text stored in the display column management table 41 is displayed in a display order stored in the display column management table 41.

Once "Input Information" is selected from the menu 38 in the list table 37 created and displayed by the information list creating section 10, an event A occurs in the computer 4. Once an item string in the information list 40 is selected, an event B occurs in the computer 4. When a user performs a manipulation for storing a still image during observation of internal part of a living body by the endoscopic observation apparatus 1, the endoscopic image filing apparatus 2 converts analog image signals from the endoscopic observation apparatus 1 to image data and outputs the image data to the computer 4. When the image data is input from the endoscopic filing apparatus 2, an event C occurs in the computer 4.

Figure 14:
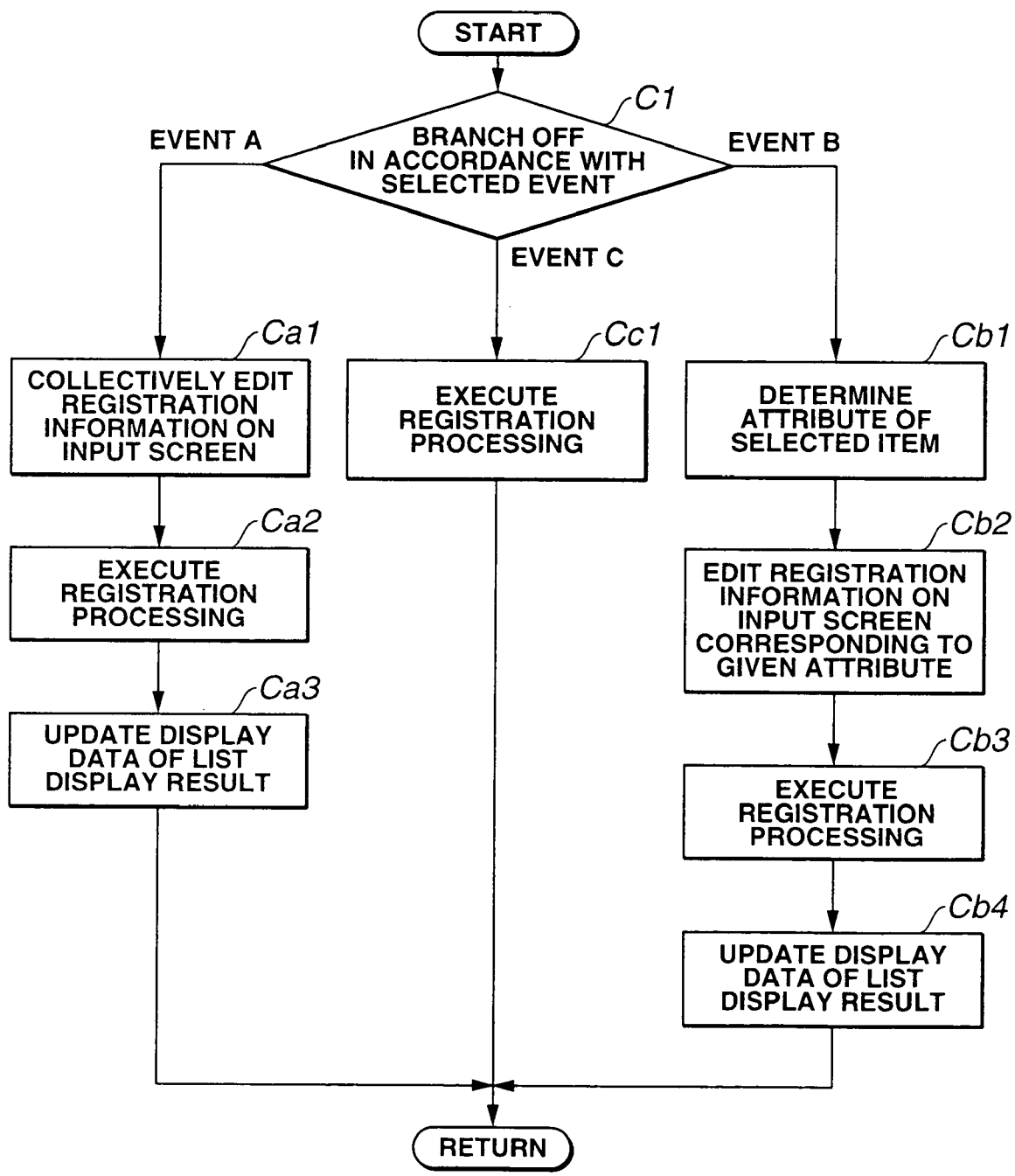

FIG. 14 is a flow diagram showing information registration processing or edit processing. At a step C1, the input selecting section 18 within the information input section 7 identifies a selected event and, if the event is an event A, determines that collective editing is selected for the information. Thus, the processing branches off to a step Ca1. If the event is an event B, the input selecting section 18 determines that editing of one item in the information list 40 is selected. Thus, the processing branches off to a step Cb1. If the event is an event C, the input selecting section 18 determines that image data output from the endoscopic filing apparatus 2 is to be newly registered with the database 14. Thus, the processing branches off to a step Cc1.

If the processing branches off to the step Ca1, the input selecting section 18 in the information input section 7 at the step Ca1 connects to the collective input section 19 and displays an information collective edit window 23 as shown in FIG. 4. On the information collective edit window 23, a patient name of patient information, an examination date of the patient information, a part name of image information, a diagnosis name of the image information and a reduced image 49 of image data of the image information are displayed in a patient name field, an examination date field, a part name field, a diagnosis name field and a reduced image field, respectively.

When an update button 27 within the information collective edit window 23 is pressed, the input selecting section 18 of the information input section 7 registers string information edited by the collective input section 19 with an item in the table in the database 14 and updates data of patient information and image information held in the computer 4 (step Ca2).

At a step Ca3, the information list creating section 10 updates the display data in the list table 37, displays the display data on the display apparatus 6 and then exits the branch processing.

If the processing branches off to the step Cc1, the input selecting section 18 of the information input section 7 at the step Cc1 newly establishes an area for holding patient information and image information in the computer 4, and image data is stored in an image data field for image information. Then, the input selecting section 18 newly registers the patient information and image information with items in the corresponding table in the database 14 and exists the branch processing.

If the processing branches off to the step Cb1, the input selecting section 18 of the information input section 7 at the step Cb1 retrieves an edit attribute corresponding to an item name at a column of a selected item from the display column management table 41 stored in the storage apparatus 5. For example, a first attribute, a second attribute and a third attribute are retrieved as an edit attribute corresponding to a diagnosis name, an edit attribute corresponding to an examination date and an edit attribute corresponding to a patient name. In this case, the first attribute is an attribute for selecting a string from choices. The second attribute is an attribute for selecting a date from a calendar. The third attribute is an edit attribute for editing a string.

At a step Cb2, the input selecting section 18 of the information input section 7 connects to a first item input section 20, a second input section 21 or a third item input section 22 in accordance with the edit attribute retrieved at the step Cb1 and causes display of an edit window. If the edit attribute is the first attribute, the input selecting section 18 is connected to the first item input section 20 and displays a string select window 24 shown in the upper part in FIG. 5. If the edit attribute is the second attribute, the input selecting section 18 is connected to the second item input section 21 and displays a date select window 26 shown in the lower part in FIG. 5. If the edit attribute is the third attribute, the input selecting section 18 is connected to the third item input section 22 and displays a string edit window 25 shown in the middle part in FIG. 5.

Once select processing or string edit processing is performed through the operation apparatus 3, the input selecting section 18 of the information input section 7 at a step Cb3 registers data updated by the first item input section 20, the second input section 21 or the third item input section 22 with an item in a corresponding table in the database 14 and updates data of the patient information and image information held in the computer 4.

At a step Cb4, the information list creating section 10 updates display data of the list table 37, displays the updated display data on the display apparatus 6 and then exits the branch processing.

FIG. 15 is a flow diagram illustrating processing for defining a region of interest to the image. At a step D1, the image region-of-interest creating section 11 retrieves image data into which a region of interest is defined and displays the image data on the display apparatus 6.

At a step D2, based on a rectangle or a free closed curve selected by a user through the operation apparatus 3, the image region-of-interest creating section 11 creates area data. The area data is two-dimensional data having a same width and height as those of the image data. If a pixel value is zero (0), a region of non-interest corresponds to the area data. If the pixel value is one (1), a region of interest corresponds to the area data.

At a step D3, the image region-of-interest creating section 11 registers region-of-interest information including area data created at the step D2 with the region-of-interest information table 17. If a region of interest is newly created at the step D2, region-of-interest information is newly established in the computer 4, and area data is stored in an area data field for region-of-interest information. After that, the region-of-interest information is newly registered with the region-of-interest information table 17.

At a step D4, the information list creating section 10 updates display data of the list table 37 and displays the updated display data on the display apparatus 6.

FIG. 16 is a flow diagram illustrating processing for calculating a characteristic value of an internal part of a region of interest. At a step E1, a characteristic value selecting section 30 of the image characteristic value creating section 9 retrieves region-of-interest information, from which a characteristic value is calculated, and image information at a higher level of the hierarchy of region-of-interest information.

At a step E2, the characteristic value selecting section 30 of the image characteristic value creating section 9 transmits area data of region-of-interest information and image data of image information to an IHb calculating section 31 or a blood-vessel-to-area-ratio calculating section 32. The IHb calculating section 31 calculates an IHb based on image data within a region of interest defined by the area data and transmits the IHb to the characteristic value selecting section 30. The blood-vessel-to-area ratio calculating section 32 calculates a ratio of blood vessels to the area based on the image data of the internal part of the region of interest defined by area data and transmits the ratio of blood vessels to the area to the characteristic value selecting section 30.

At a step E3, the characteristic value selecting section 30 of the image characteristic value creating section 9 updates region-of-interest information by using the IHb calculated at the step E2 as the first characteristic value and registers region-of-interest information with the region-of-interest information table 17. Alternatively, the characteristic value selecting section 30 updates region-of-interest information by using the ratio of blood vessels to the area calculated at the step E2 as a second characteristic value and registers region-of-interest information with the region-of-interest information table 17.

At a step E4, the information list creating section 10 updates display data of the list table 37 and displays the updated data on the display apparatus 6.

Figure 17:
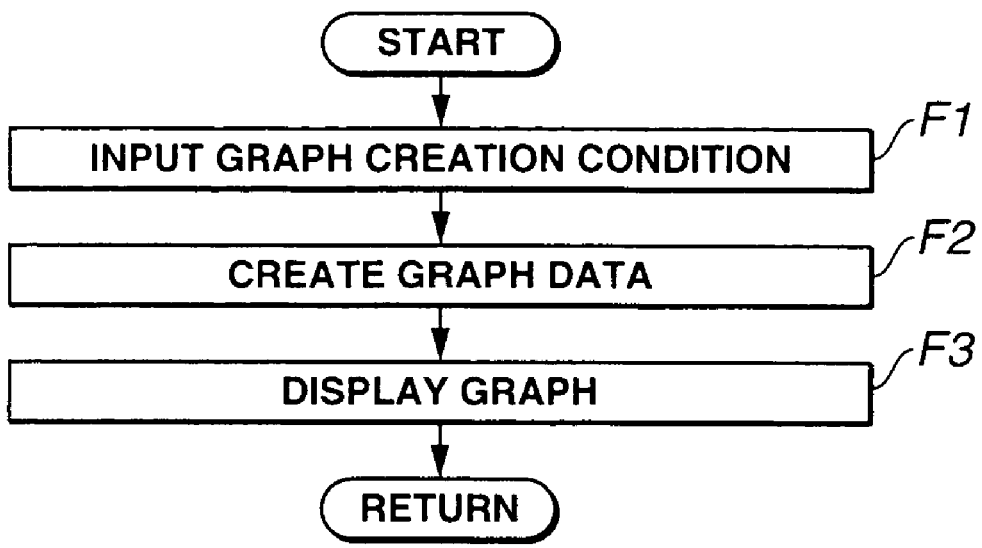

FIG. 17 is a flow diagram illustrating graph display processing. At a step F1, the graph executing section 13 displays the graph creation condition input window 33 shown in FIG. 8.

On the graph creation condition input window 33, a type of a graph, a category item, and data values to be graphed are defined as a result of a selection operation by a user through the operation apparatus 3.

At a step F2, the graph executing section 13 creates a graph based on a defined condition. At a step F3, the graph executing portion 13 causes the display apparatus 6 to display the created graph.

Figure 18:
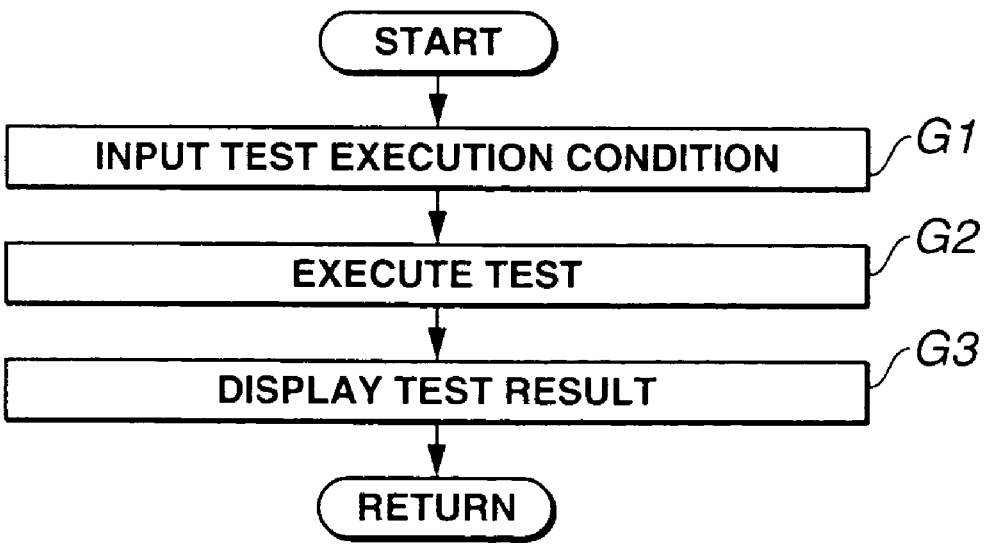

FIG. 18 is a flow diagram illustrating test executing processing. At a step G1, the test executing section 12 displays the test execution condition input window 35 shown in FIG. 9.

Here, a user may define a test condition by performing selection through the operation apparatus 3 and press an execution button 36 within the test execution condition input window 35. Then, at a step G2, the test executing section 12 determines a test procedure by following a flow shown in FIG. 19 and performs test processing based on the determined test procedure.

At a step G3, the test executing section 12 causes the test result shown in FIG. 20 to be displayed on the display apparatus 6.

Figure 19:
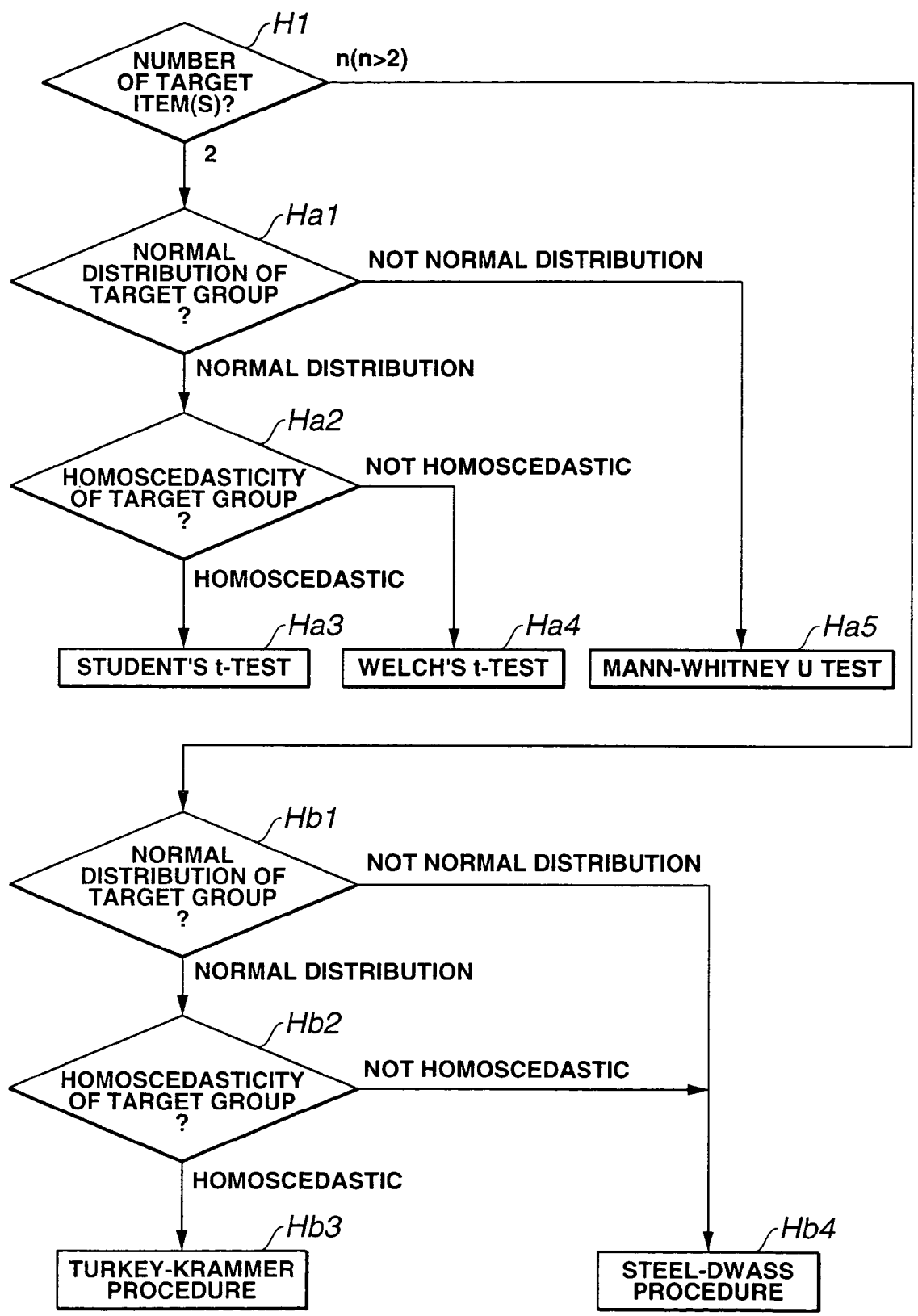

The processing for determining a test procedure at the step G1 in the flow diagram shown in FIG. 19 will be described.

At a step H1, the test executing section 12 counts the number of category items held by patient information, image information or region-of-interest information held by the computer 4 among category items selected at the step G1. If the number of category item is lower than 2, test cannot be executed. Thus, processing is stopped here. If the number of category item is equal to 2, data values selected at the step G1 are collected and are grouped for each of the kinds, and the processing goes to a step Ha1. If the number of category item are higher than 2, data values selected at the step G1 are collected and are grouped for each of the kinds. Thus, the processing goes to a step Hb1.

For example, on the test execution condition input window 35 in FIG. 9, when a diagnosis name is selected as a category item and a characteristic value 1 is selected as a data value, and if the groups of patient information, image information and region-of-interest information held by the computer only have "cancer" or "normal" as diagnosis names being category items, the number of category item is counted as 2. Therefore, values of the first characteristic value of the group having "cancer" or "normal" as diagnosis names are collected, and two numeric value groups are formed.

Next, a processing flow subsequent to the advance to a step Ha1 will be described. At the step Ha1, the test executing section 12 determines whether or not a distribution of each of the groups can be regarded as a standard distribution by Shapiro-Wilks test or Kolmogorov-Smirnov test. Both of the test procedures are widely known as test procedures for a normal distribution.

If the distributions of all of the groups cannot be regarded as the normal distribution, the processing advances to a step Ha5 where Mann-Whitney U Test is determined as a test procedure to be implemented. If so, the processing advances to a step Ha2.

The Mann-Whitney U Test is widely known as a test procedure for a difference between mean values where a population is not the normal distribution (that is, nonparametric).

At the step Ha2, the test executing section 12 determines whether the distribution of each of the groups can be regarded as being homoscedastic or not by F-test. F-test is widely known as a homoscedasticity test procedure for two groups.

If so, the processing goes to a step Ha3 where Student's t-test is determined as a test procedure to be executed. If not, the processing goes to a step Ha4 where Welch's t-test is determined as a test procedure to be executed.

Student's t-test is widely known as a test procedure for a difference between mean values to be used when a population has a normal distribution and is homoscedastic.

Welch's t-test is widely known as a test procedure for a difference between mean values to be used when a population has a normal distribution.

Next, a processing flow subsequent to the determination for the advance to a step Hb1 will be described. At the step Hb1, the test executing portion 12 determines whether a distribution of each of the groups can be regarded as the normal distribution by Shapiro-Wilks Test or Kolmogorov-Smirnov Test.

If the distributions of all of the groups cannot be regarded as the normal distribution, the processing goes to a step Hb4 where Steel-Dwass procedure is determined as a test procedure to be executed.

If the distributions of all of the groups can be regarded as the normal distribution, the processing goes to a step Hb2. At the step Hb2, the test executing section 12 determines whether the distribution of each of the groups can be regarded as being homoscedastic or not by Bartlett procedure or Levene procedure. Bartlett procedure and Levene procedure are widely known as homoscedasticity test procedures for n groups (n>2).

If so, the processing goes to a step Hb3 where Tukey-Kramer procedure is determined as a test procedure to be executed. If not, the processing goes to a step Hb4 where Steel-Dwass procedure is determined as a test procedure to be executed.

Tukey-Krammer procedure is widely known as a test procedure for a difference between mean values of n groups when a population is homoscedastic. Steel-Dwass procedure is widely known as a test procedure for a difference of mean values of n groups when a population cannot be regarded as having a normal distribution (nonparametric).

With these advantages as described above, a user only needs to select a target to be tested to execute an optimum test procedure for the test target.

(Advantages)

An optimum test procedure can be derived and be executed based on results from determination of the normality or homoscedasticity of a test target, and an improper selection of a test procedure by a beginner can be prevented. An optimum input method can be provided for each type and characteristic of an item to be input and edited. Creating and displaying a list table of images and characteristic values facilitates the determination on whether characteristic values of images can be calculated or not with reference to the list table.

According to the first embodiment, an optimum test procedure can be selected automatically. Thus, a work effort therefor can be reduced, and an improper selection of a test procedure can be prevented so that an accurate test result can be obtained. Since an optimum input method for a type of an item to be input and edited can be provided, the operability can be improved. Furthermore, since display with high viewability can be provided, misoperations can be prevented and the operability can be improved thereby.

While an IHb and ratio of a blood vessel to an area calculated from an endoscopic image are used as a test target according to this embodiment, a test target is not limited to those in the medical field. Generally, the same advantages can be obtained as far as the test target is a value which can be tested.

Variation Example of First Embodiment

Next, a variation example of the first embodiment will be described with reference to FIG. 21. A display column management table 41 stored in the storage apparatus 5 can be edited freely by a user. Furthermore, a user can freely add an item into the patient information table 15, image information table 16 or region-of-interest information table 17 in the database 14.

Figures 21, 22:
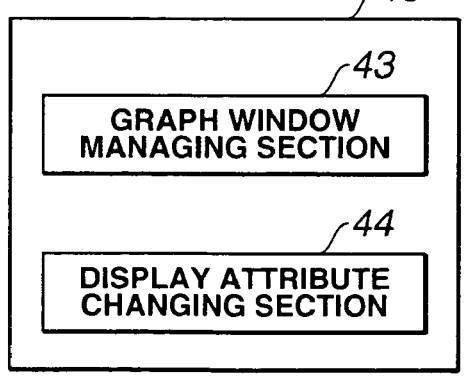

Since the free addition of items is allowed, items having a same column name are created at different hierarchical levels as shown in FIG. 21, for example (FIG. 21 shows an example that display text, "name of part", may be created for an image and a region of interest), and a name of a column only accepting input of numeric values is created such that the name can tell the input of strings is allowed for the column (while an item having "used drug" as display text is created in the example in FIG. 21. A numeric value code for a used drug is defined to input therein, and input of a string is not assumed. Since only numeric values is valid, confusion may be caused in inputting information by a user).

(Construction)

As described above, the information list creating section 10 can determine display text and a display order of column items in the information list 37 based on the display column management table 41 stored in the storage apparatus 5. The information list creating section 10 can further determine a display color of display text of a header of the column item in the information list 37 based on a display attribute in the display column management table 41 and display an icon in accordance with a hierarchical level at the beginning of display text of the header of the column item in the information list 37.

In this variation example according to this embodiment, a display color is red when a display attribute of a given display column is "text", blue when a display attribute of a given display column is "date" and green when a display attribute of a given display column is "numeric value". When a hierarchical level of a given display column is "patient", an icon having a letter "PP" is displayed at the beginning of the string of the header of the column item. When a hierarchical level of a given display column is "image", an icon having a letter "I" is displayed at the beginning of the string of the header of the column item. When a hierarchical level of a given display column is "region of interest", an icon having a letter "F" is displayed at the beginning of the string of the header of the column item.

(Operation)

Like the first embodiment, at a step B4 in the flow diagram in FIG. 13 according to this variation example, the information list creating section 10 uses the display column management table 41 stored in the storage apparatus 5 in order to display, in the information list 37, sets of patient information, image information and region-of-interest information held in the computer 4.

In order to create a column, display text stored in the display column management table 41 is displayed in a display order stored in the display column management table 41. Here, a display color of the text is determined based on display attribute information stored in the display column management table 41. Furthermore, an icon is displayed at the beginning of the display text of the header in the information list 37 based on hierarchical information stored in the display column management table 41.

(Advantage)

Misidentification of an information item on a list table can be prevented.

Second Embodiment

Since a second embodiment is the same as the first embodiment except for the construction of the graph executing section 13, the difference will be only described. The same reference numerals are given to the same components, and the description thereof will be omitted herein.

(Construction)

FIG. 22 shows a block diagram of the graph executing section 13 according to the second embodiment. The graph executing section 13 further includes a graph window management section 43 and a display attribute change section 44.

The display attribute change section 44 changes a display form (that is, display forms of a marker and text) on a created graph under a condition selected on a graph display setting change window 45 shown in FIG. 23.

The graph window management section 43 holds a graph display setting table 47 shown in FIG. 24 in the computer 4 for each created graph. The graph display setting table 47 records, for graph display, category class names, marker forms, marker sizes, marker colors and a display order of category class names. The graph display setting table 47 further records a title, a legend, and fonts and sizes of strings for the X-axis and Y-axis of a graph.

The graph window management section 43 causes the storage apparatus 5 to store a marker setting table 48 shown in FIG. 25 for each category item. The marker setting table 48 has associations between category items and a category class name, a marker form, a marker size, a marker color and display order of category classes. A marker setting table 48 is used as default settings for category item in order to create a graph.

(Operation)

First of all, an operation for creating a new graph will be described. At a step F2 in FIG. 17, in order to create graph data, the graph executing section 13 reads the marker setting table 48 from the storage apparatus 5 and creates a graph corresponding to a category item selected on the graph creation condition input window 33 based on settings in the marker setting table 48.

Figure 26:
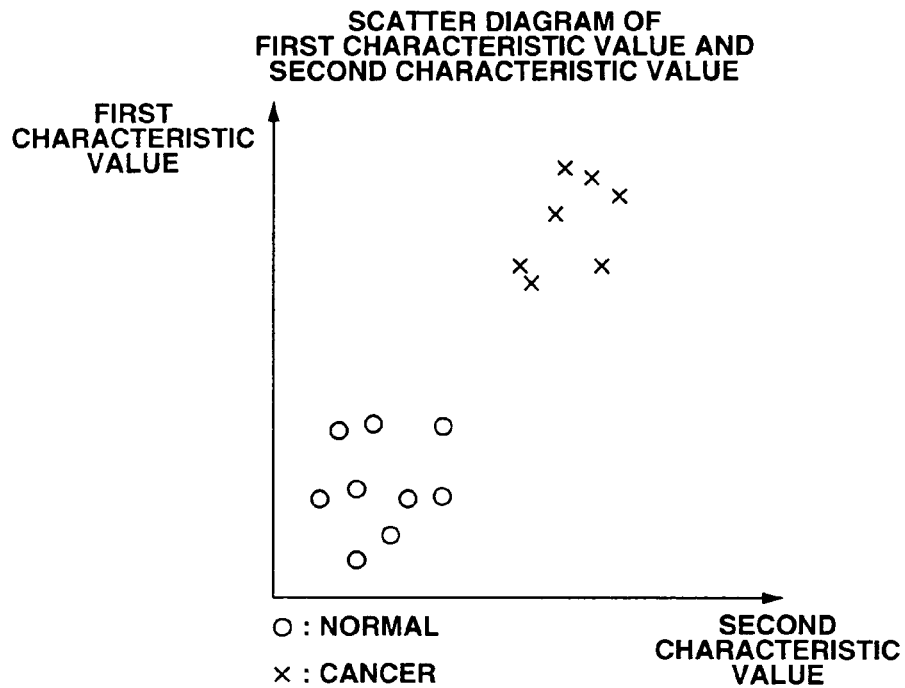

A marker on a graph is displayed in form, size and color defined in the marker setting table 48. Category class names are displayed in a legend in a display order defined in the marker setting table 48. A display example in a two-dimensional scatter diagram is shown in FIG. 26.

Figure 27:
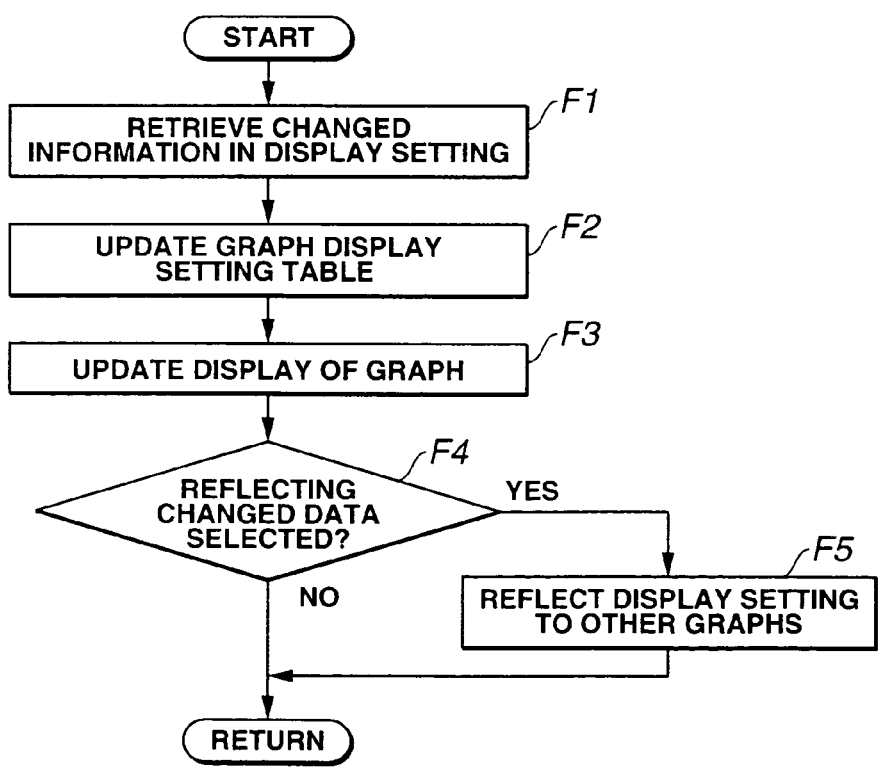

Next, changing data to be displayed on a created graph will be described. Once a user instructs to change data to be displayed on a created graph, processing therefor is performed by following a flow shown in FIG. 27.

At a step F'1, the display attribute change section 44 causes the display apparatus 6 to display the graph display setting change window 45 shown in FIG. 23 and prompts a user to input data to be changed. When an execution button 46 on the graph display setting change window 45 is pressed, the display attribute change section 44 retrieves selected data on the graph display setting change window 45.

On the graph display setting change window 45, a form, size or color can be selected as a change target in settings of a marker to be displayed on a graph, and a font and size can be selected as change target for a setting of a text display form. Furthermore, whether changed data is reflected to other graphs or not can be selected thereon.

At a step F'2, the graph window management section 43 updates data on the graph display setting table 47 regarding a graph selected as a change target at the step F'1.

At a step F'3, the display attribute change section 44 updates display data regarding a graph selected as a change target at the step F'1 based on data on the graph display setting table 47 held by the graph window management table 43.

At a step F'4, the display attribute change section 44 judges whether "changed data is reflected to other graphs" has been selected or not on the graph display setting change window 45 at the step F'1.

If "changed data is reflected to other graphs" has been selected, the processing goes to a step F'5 where display data on the other graph display setting tables 47 are updated based on the data on the graph display setting table 47 changed at the step F'1. In other words, the graph window management section 43 causes the display attribute change section 44 to update all of held graph display data, and the display attribute change section 44 updates display data on all created graphs based on data on the graph display setting table held in the graph window management section 43. The display attribute change section 44 updates information on the marker setting table 48 based on data on the graph display setting table 47 changed at the step F'1.

(Advantages)

Since graphs are created each having a legend and graph markers with a display form and legend item defined as predetermined values corresponding to category items and displayed in order, uniform graph display can be achieved. Furthermore, since a display order of a graph marker display form and legend items is defined uniformly for multiple graph displays, the effort for the definition can be reduced, and the misidentification due to differences in display form among graphs can be reduced.

Third Embodiment

A third embodiment is the same as the first embodiment except that the construction of the graph executing section 13 and the test executing section 12 are different. Thus, differences therebetween will be only described, and the same reference numerals are given to the same components, the descriptions of which will be omitted herein.

(Construction)

The graph executing section 13 displays a graph creation condition input window 33 shown in FIG. 28. A difference in construction of the graph executing section 13 from the one according to the first embodiment is that the graph creation condition input window 33 further includes a radio button A50, a radio button B51 and a radio button C52.

Pressing the radio button A50 instructs the graph executing section 13 to change a selected item from a graph type, category items and first and second data values to an item just selected on the graph creation condition input window 33.

Pressing the radio button B51 instructs the graph executing section 13 to change a selected item from category items and first and second data values to an item just selected on the graph creation condition input window 33 for a currently selected graph type.

Pressing the radio button C52 instructs the graph executing section 13 to change a selected item from category items and a first data value to an item just selected on the test execution condition input window 35.

The test executing section 12 displays the test execution condition input window 35 shown in FIG. 29. A difference between the test executing section 12 and the one according to the first embodiment is that the test execution condition input window 35 further includes a radio button D55 and a radio button E56.

Pressing the radio button D55 instructs the test executing section 12 to change a selected item from category items and a data value to an item just selected on the test execution condition input window 35.

Pressing the radio button E56 instructs the test executing section 12 to change a selected item from category items and a data value to an item just selected on the graph creation condition input window 33. In this case, a first data value on the graph creation condition input window 33 is equivalent in context to a data value on the test execution condition input window 35.

The storage apparatus 5 stores a setting history table 58 shown in FIG. 30. The setting history table 58 records setting types, set procedures, set category items, set first values and set second data values, which are associated with each other.

The graph executing section 13 reads the setting history table 58 and defines a selected item on the graph creation condition input window 33 based on data on the setting history table 58 and records the selected item on the graph creation condition input window 33 into the setting history table 58.

The test executing section 12 reads the setting history table 58 and defines a selected item on the test execution condition input window 35 based on data on the setting history table 58 and records the selected item on the test execution condition input window 35 into the setting history table 58.

When a selected category item on the test execution condition input window 35 or the graph creation condition input window 33 is changed, the test executing section 12 and the graph executing section 13 updates a display of an item group to be displayed in data values, first data values or second data values.

(Operation)

Figure 31:
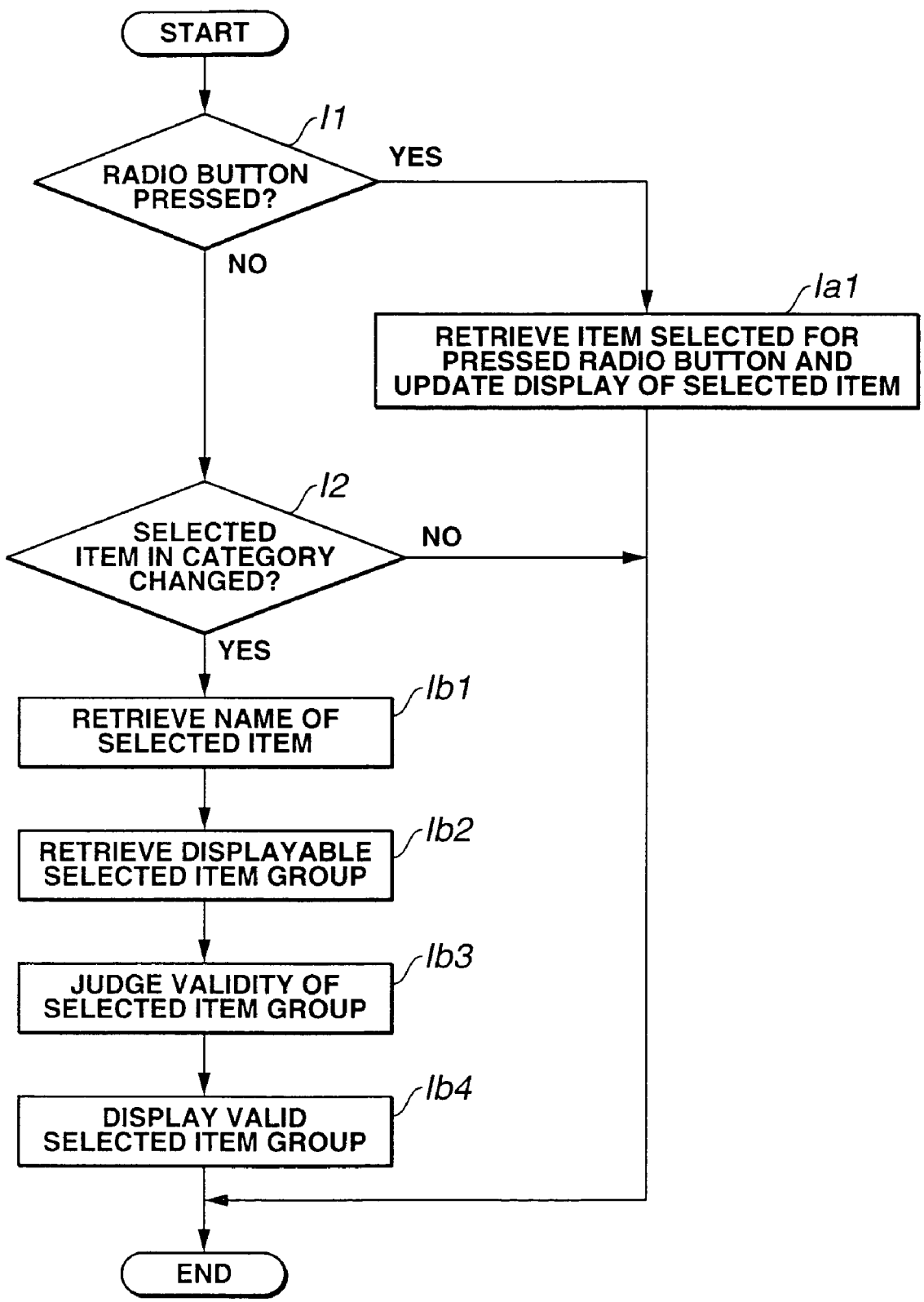

By following a flow in FIG. 31, the graph executing section 13 and the test executing section 12 changes a selected item on the graph creation condition input window 33 or the test execution condition input window 35 and an item group to be displayed.

The flow in FIG. 31 is repeatedly performed upon display of the graph creation condition input window 33 or the test execution condition input window 35.

At a step I1, the test executing section 12 or the graph executing section 13 judges whether any radio button has been pressed or not. If any radio button has been pressed, the processing branches off to a step Ia1. If no radio button has been pressed, the processing branches off to a step I2.

At the step I2, the test executing section 12 or the graph executing section 13 judges whether a selected category item has been changed by a manipulation by a user. If a selected category item has been changed, the processing branches off to a step Ib1. If a selected category item has not been changed, the processing ends.

Next, processing at the step Ia1 and subsequent steps will be described. At the step Ia1, the test executing section 12 or the graph executing section 13 judges the type of the pressed radio button.

If the pressed radio button is the radio button A50, the graph executing section 13 changes, based on the setting history table 58 and with reference to a row having "graph" as the type, the procedure, category, first data value and second data value of the row of the setting history table to the selected items of the procedure, category, first data value and second data value on the graph creation condition input window 33.

If the pressed radio button is the radio button B51, the graph executing section 13 changes, based on the setting history table 58 and with reference to a row having a same one as the type currently selected as the procedure on the graph creation condition input window 33, the category, first data value and second data value of the row of the setting history table to the selected items of the category, first data value and second data value on the graph creation condition input window 33.

If the pressed radio button is the radio button C52, the graph executing section 13 changes, based on the setting history table 58 and with reference to a row having "test" as a type, the category, first data value and second data value of the row of the setting history table to the selected items of the category and first data value on the graph creation condition input window 33.

Similarly, when the pressed radio button is the radio button D55 or the radio button E56, the test executing section 13 performs the same processing and changes the selected item of the category and data values on the test execution condition input window 35. After these steps, the data to be displayed on the display apparatus 6 is updated, and the processing ends.

Next, steps including the step Ib1 will be described. At the step Ib1, the test executing section 12 or the graph executing section 13 retrieves a newly selected item for a category on the test execution condition input window 35 or the graph creation condition input window 33.

At a step Ib2, the test executing section 12 or the graph executing section 13 retrieves all display strings defined at a row having numeric display attributes from the display column management table 41 (refer to FIG. 11) stored in the storage apparatus 5. For example, if display strings are defined as shown in FIG. 11, a first characteristic value, second characteristic value and patient age are retrieved.

At a step Ib3, the test executing section 12 or the graph executing section 13 retrieves a set of patient information, image information and region-of-interest information held in the computer 4 and judges whether or not valid values are defined for items corresponding to the display strings retrieved at the step Ib2 with respect to the all retrieved information sets. Each display string has a counter, and the number of sets of information having valid values set is counted and is recorded in the counter.

At a step Ib4, the test executing section 12 refers to the counter value of the display string recorded at the step Ib3 and displays a display string having the counter value larger than the number (10 in this embodiment) allowing a significant test as a selected item group at a data value column on the test execution condition input window 35.

Alternatively, at the step Ib4, the graph executing section 13 refers to the counter value of the display string recorded at the step Ib3 and displays a display string having the counter value equal to or larger than one (1) as a selected item group at fields for first and second data values on the graph creation condition input window 33. After these steps, the display data on the display apparatus 6 is updated, and processing ends.

After the display of a test result by the test executing section 12 or the display of a graph by the graph executing section 13, the test executing section 12 or the graph executing section 13 substitutes an item selected on the test execution condition input window 35 or the graph creation condition input window 33 into the setting history table 58 stored in the storage apparatus and updates the data in the setting history table 58.

(Advantages)

Since a past history information is reused, the operational load can be reduced. Furthermore, since a history condition for processing independent of a procedure is reused, the operational load for continuously executing different procedures can be reduced.

Since choices for items which are defined but not available are not displayed, improper selections can be prevented, and the operability of selection operations can be improved.

Fourth Embodiment

A fourth embodiment is constructionally different in that an endoscopic observation apparatus according to the first embodiment further includes an image select switch. Therefore, the difference is only described, and the same reference numerals are given to the same components, the descriptions of which will be omitted herein.

(Construction)

Figures 32, 33:
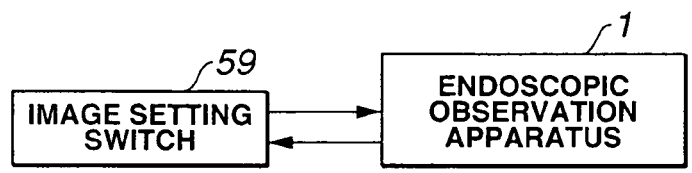
FIGS. 32 to 34 relate to a fourth embodiment.

According to this embodiment, as shown in a block diagram in FIG. 32, the endoscopic observation apparatus 1 according to the first embodiment further includes an image select switch 59.

The image select switch 59 is constructed as a switch to be turned on/off by a user during endoscopic observation on a living body, such as a foot switch, a switch in an endoscope operating section and a microswitch removably attached to the endoscope operating section.

The ON/OFF state of the image select switch 59 is transmitted to the computer 4 through the endoscopic filing apparatus 2.

As shown in FIG. 33, the image information table 16 in the database 14 according to this embodiment further includes an importance field for recording importance of an image. The importance field stores one (1) indicating an image having higher importance or zero (0) indicating an image having lower importance.

An image region-of-interest creating section 11 selects a region of interest in response to a manipulation on the operation apparatus 3 and creates a region of interest based on predetermined coordinates values.

When the importance field of the image information has 1, the information list creating section 10 displays a frame around a reduced image 49 and informs a user of that the reduced image has high importance.

(Operation)

An image determined by a user as important (called important image hereinafter) is stored in the information processor 100 will be described. An operation of the information processor 100 in relation to a work referring to the important image for an image diagnosis after an examination, such as a conference.

First of all, processing for registering an important image will be described. The endoscopic filing apparatus 2 transmits image data and an ON/OFF state of the image select switch 59 to the computer 4.

Here, when the image select switch 59 is ON, a user may observe a living body by increasing a scaling factor of the endoscopic observation apparatus 1 and may store a still image of the enlarged display image of a lesion. Then, the endoscopic filing apparatus 2 outputs to the computer 4 information that the image select switch 59 is ON and image data based on analog image signals output from the endoscopic observation apparatus 1.

Figure 34:
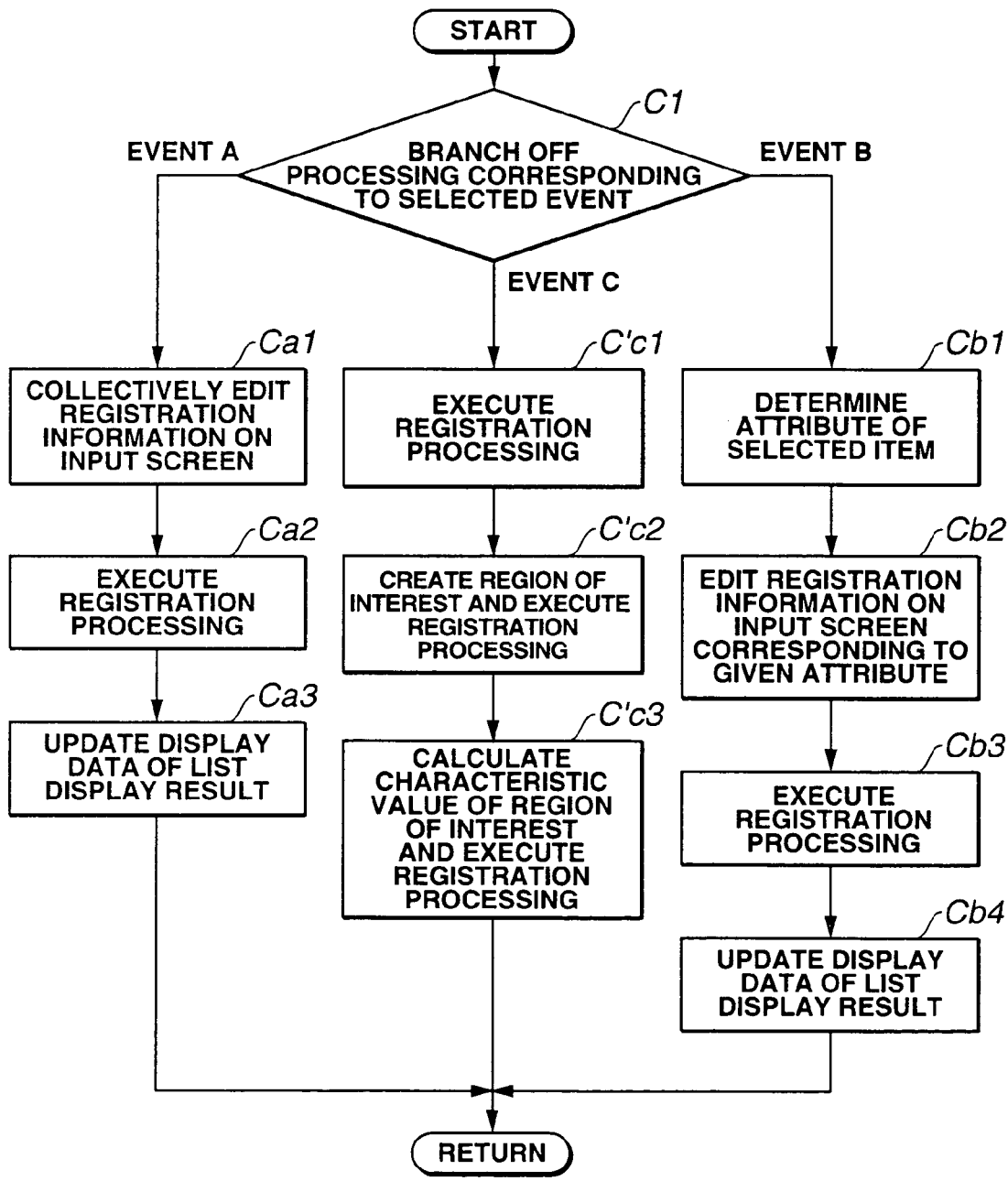

While the subsequent steps follow the flow diagram shown in FIG. 14 according to the first embodiment, the subsequent steps follow a flow diagram shown in FIG. 34 according to this embodiment. The difference will be described below.

At a step C'c1, the input selecting section 18 of the information input section 7 newly establishes an area for holding patient information and image information in the computer 4 and stores an image data in an image data field for image information. The input selecting section 18 stores 1 if the image select switch 59 is ON or 0 if OFF in an importance field for image information. After that, patient information and image information are newly registered with the items in the table in the database 14.

Next, at a step C'c2, the image region-of-interest creating section 11 performs processing for defining a region of interest for image data.

The processing for defining a region of interest according to this embodiment is substantially similar to as the processing following the flow diagram shown in FIG. 15 according to the first embodiment. However, a step D2 in the flow diagram shown in FIG. 15 is different and therefore will be described below.

At the step D2, the image region-of-interest creating section 11 creates a region of interest including predetermined coordinates. As shown in the reduced image 49 in FIG. 10, an image picked up by the endoscopic observation apparatus 1 can be divided into a right area for displaying an image of an internal part of a living body and a left area for displaying accessory information such as patient information. The area displaying an in-body image of an internal part of the living body is fixed in the creating endoscopic observation apparatus 1. The image region-of-interest creating section 11 creates a region of interest by using the coordinate information.

Next, at a step C'c3, the image characteristic value creating section 9 calculates a characteristic value of the region of interest created at the step C'c2.

The calculation of a characteristic value according to this embodiment is substantially similar to the step in the flow diagram shown in FIG. 16 according to the first embodiment. However, the steps E2 and E3 are different in the flow diagram shown in FIG. 16 and will be therefore described below.

At the step E2, the characteristic value selecting section 30 of the image characteristic value creating section 9 transmits area data of region-of-interest information and image data of image information to the IHb calculating section 31 and blood-vessel-to-area calculating section 32 of the image characteristic value creating section 9 and calculates an IHb and a ratio of blood vessels to an area.

At the step E3, the characteristic value selecting section 30 of the image characteristic value creating section 9 updates region-of-interest information by using the IHb calculated at the step E2 as a first characteristic value and updates region-of-interest information by using the ratio of the blood vessels to the area calculated at the step E2 as a second characteristic value. Then, the characteristic value selecting section 30 registers the region-of-interest information with the region-of-interest information table 17.

From these steps, image data upon storage in the endoscopic observation apparatus 1 and importance of the image data are recorded in the information processor 100.

Next, processing for viewing an important image will be described. A difference in viewing an important image between this embodiment and the first embodiment is the operation at a step B4 in the flow diagram shown in FIG. 13.

According to this embodiment, at the step B4, the information list creating section 10 displays the reduced image 49 with a rectangular frame if the importance of given image information is 1 and displays the reduced image 49 without the rectangular frame if the importance is 0.

(Advantages)

The work efficiency can be improved since a predetermined region of interest and a characteristic value are created for an image that a user determines as an important image in registering with an information processor. Furthermore, since an image having high importance is displayed with a frame according to this embodiment, an effort for searching an image having high importance can be saved.

Fifth Embodiment

The fifth embodiment is substantially similar to the fourth embodiment and is only different in that the computer according to the fourth embodiment further includes a related-information searching section. Therefore, differences will be only described, and the same reference numerals are given to the same components, the descriptions of which will be omitted.

(Construction)

Figure 35:
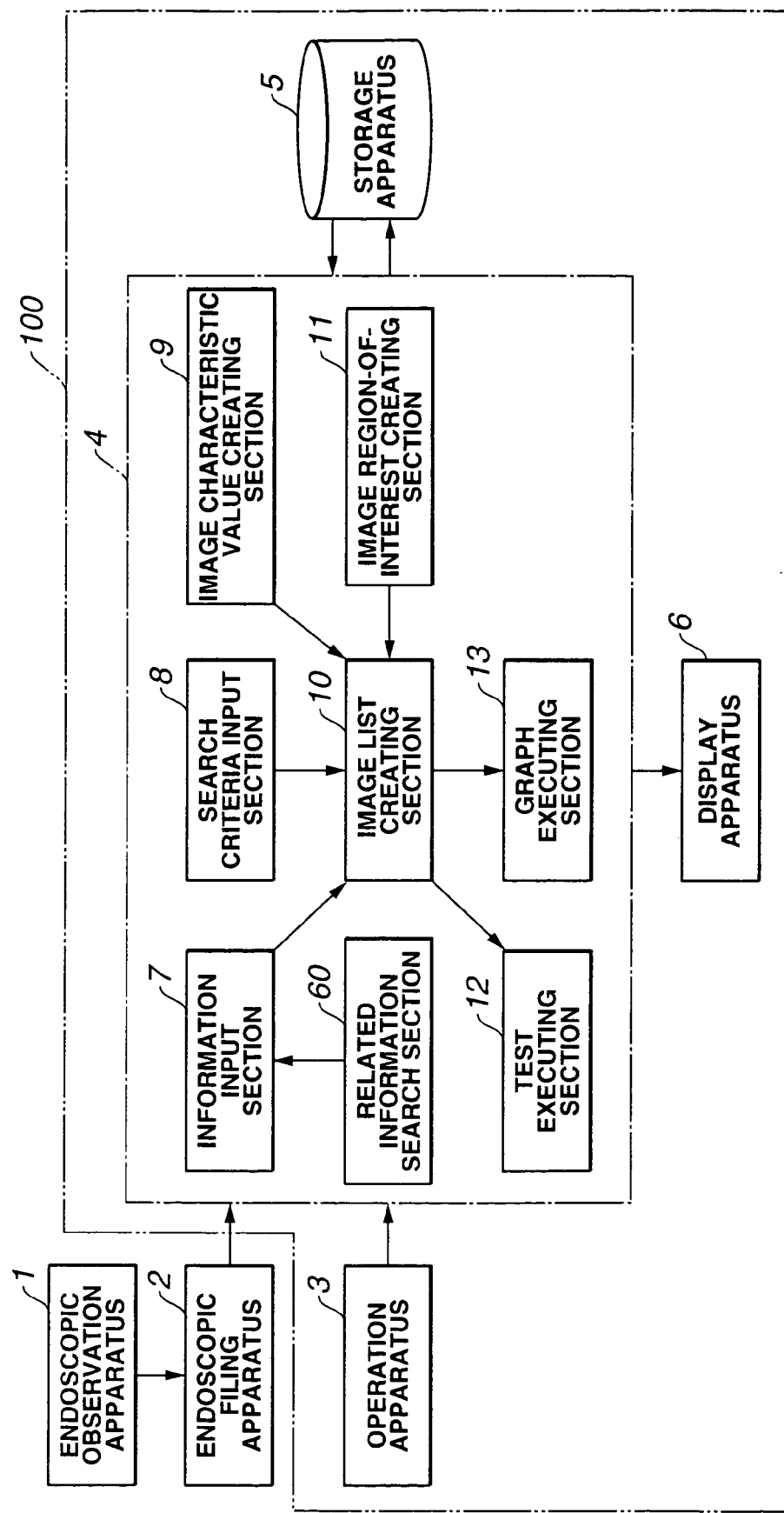
FIGS. 35 to 37 relate to a fifth embodiment of the invention.

As shown in a block diagram in FIG. 35, according to this embodiment, the computer 4 according to the fourth embodiment further includes a related-information searching section 60.

The related-information searching section 60 searches by using a range of a characteristic value or an image ID as a search key.

When a range of a characteristic value is used as a search key, the related-information searching section 60 searches the database 14 having a combination of the patient information table 15, the image information table 16 and the region-of-interest information table 17. Thus, the related-information searching section 60 retrieves and holds in the computer 4 a set of focus information, image information at a higher hierarchical level and patient information at a still higher hierarchical level having characteristic values in specific ranges.

The related-information searching section 60 uses AND of multiple specified characteristic value ranges as a search key when multiple characteristic value ranges are specified for each characteristic value procedure.

The image information table 16 of the database 14 according to this embodiment further includes a related-image ID field for recording an image ID of image information highly related with given image information.

When an image ID is used as a search key, the related-information searching section 60 searches a combination of the patient table 15 and the image table 16. Thus, the related-information searching section 60 creates and holds a set of image information having a specified image ID and patient information at a higher hierarchical level.

Figure 36:
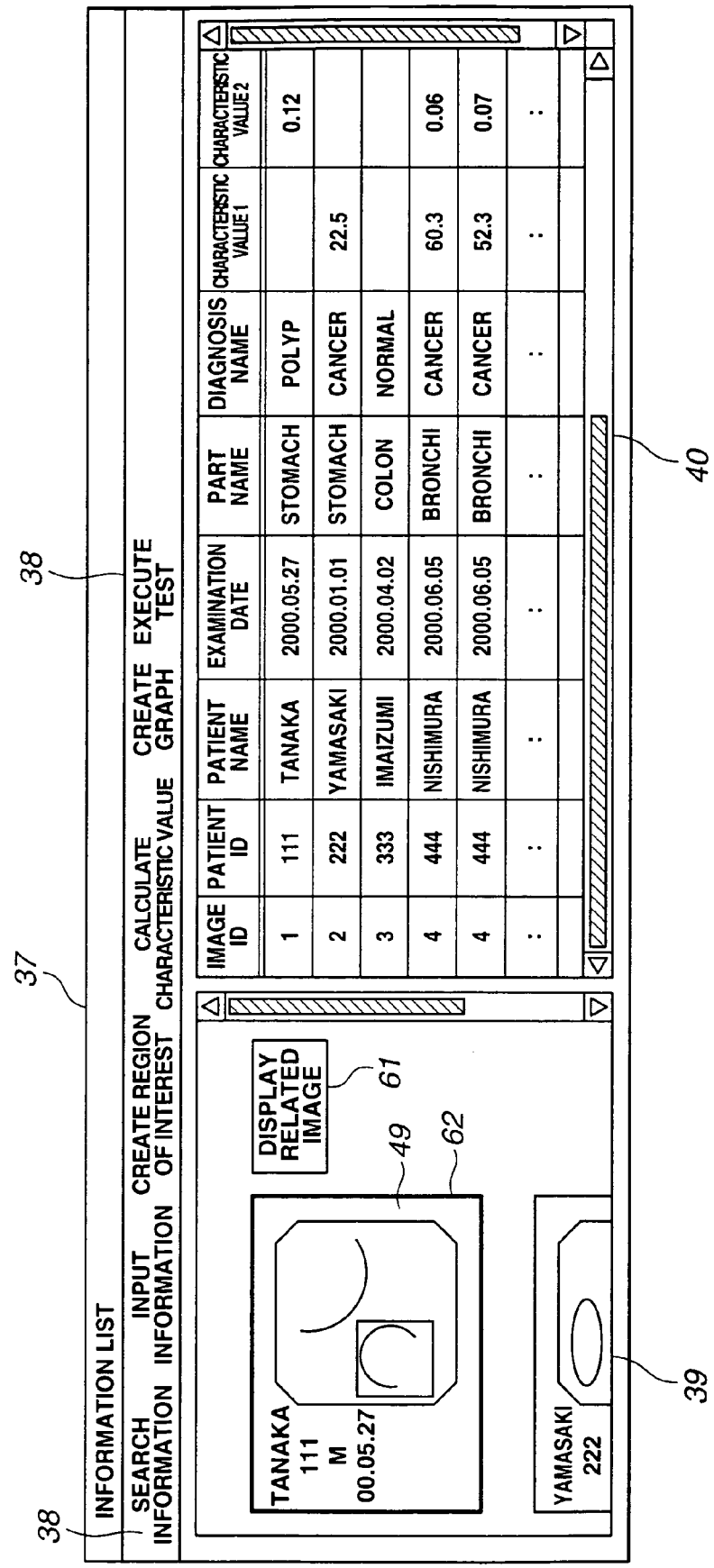

FIG. 36 shows an example of the list table 37 created by the information list creating section 10 according to this embodiment. Like the fourth embodiment, importance is given to image information, and a frame 62 is displayed with the reduced image 49 of an important image having 1 as importance. Furthermore, a related-image display button 61 is displayed by the side of the reduced image 49 of the important image.

Once a user presses the related-image display button 61, the information list creating section 10 transmits a value stored in the related-image ID field of the image information of the reduced image 49 to the related-information searching section 60. The related information searching section 60 searches the database 14 by using an image ID as a key. The information list creating section 10 displays, on the display apparatus 6 as an image, image data in the image data field for the image information retrieved by the related-information searching section 60.

(Operation)

An operation by the information processor 100 will be described in relation to a process by a user for displaying an image related to an important information.

This embodiment is different from the fourth embodiment in processing for registering an important image and processing for viewing an important image.

Figure 37:
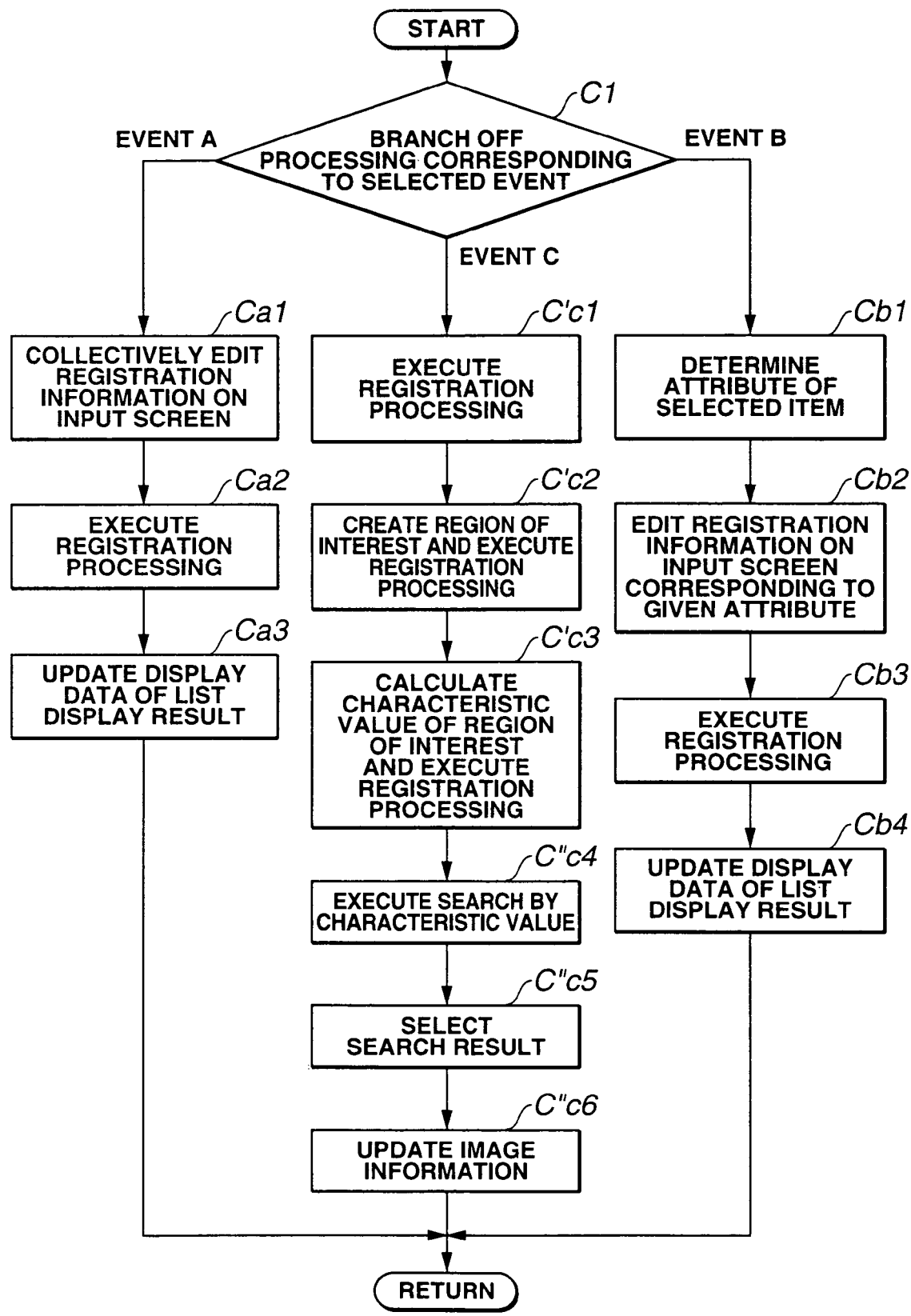

First of all, the processing for registering an information image will be described. While the processing follows the flow diagram shown in FIG. 34 according to the fourth embodiment, the processing follows a flow diagram shown in FIG. 37 according to this embodiment. The difference will be described below.

The processing from the steps C'c1 to C'c3 is the same as that of the fourth embodiment.

At a step C"c4, the information input section 7 adjusts a predetermined-value for a characteristic value calculated at the step C'c3. Thus, the information input section 7 creates a characteristic value range and transmits the characteristic value range to the related-information searching section 60. The related-information searching section 60 searches the database 14 by using the received characteristic value range as a search key and stores a set of region-of-interest information, image information and patient information in the computer 4.

At a step C"c5, the information input section 7 selects one of sets of region-of-interest information, image information and patient information retrieved and held by the related-image searching section 60 at the step C"c4 under:

Condition 1: A value stored in an importance field of image information is 1,

Condition 2: A valid value is stored under a diagnosis name, and

Condition 3: A valid value is stored under a patient name.

At a step C"c6, the information input section 7 stores an image ID within image information of the information set selected at the step C"c5 into a related-image ID field within image information registered at the step C'c1 and registers the image information with the database 14.

Next, processing for viewing an important image will be described. A difference in viewing an important image between this embodiment and the fourth embodiment or the first embodiment is the step B4 in the flow diagram shown in FIG. 13. The other steps are the same as those of the fourth embodiment or first embodiment.

At the step B4 according to this embodiment, the information list creating section 7 further includes a related-image display button 61 by the side of the reduced image 49 when a valid value is stored as a related-image ID of given image information upon display of the reduced image 49.

Once a user presses the related-image display button 61, the information list creating section 10 transmits the value stored in the related-image ID field of the image information of the reduced image 49 to the related-information searching section 60. The related-information searching section 60 searches by using the image ID as a key. The information list creating section 10 displays, on the display apparatus 6 as an image, image data in the image data field of the image information retrieved by the related-information searching section 60.

(Advantage)

The operational responsivity can be improved since highly related information is searched and is associated with an important image in advance.

Sixth Embodiment

A sixth embodiment is substantially similar to the first embodiment and is only different in construction that an information processor is connected to a LAN connecting to a characteristic value calculating procedure supply server and further includes a download section and characteristic value update section in a computer. Differences will be only described, and the same reference numerals are given to the same components, the descriptions of which will be omitted herein.

(Construction)

Figure 38:
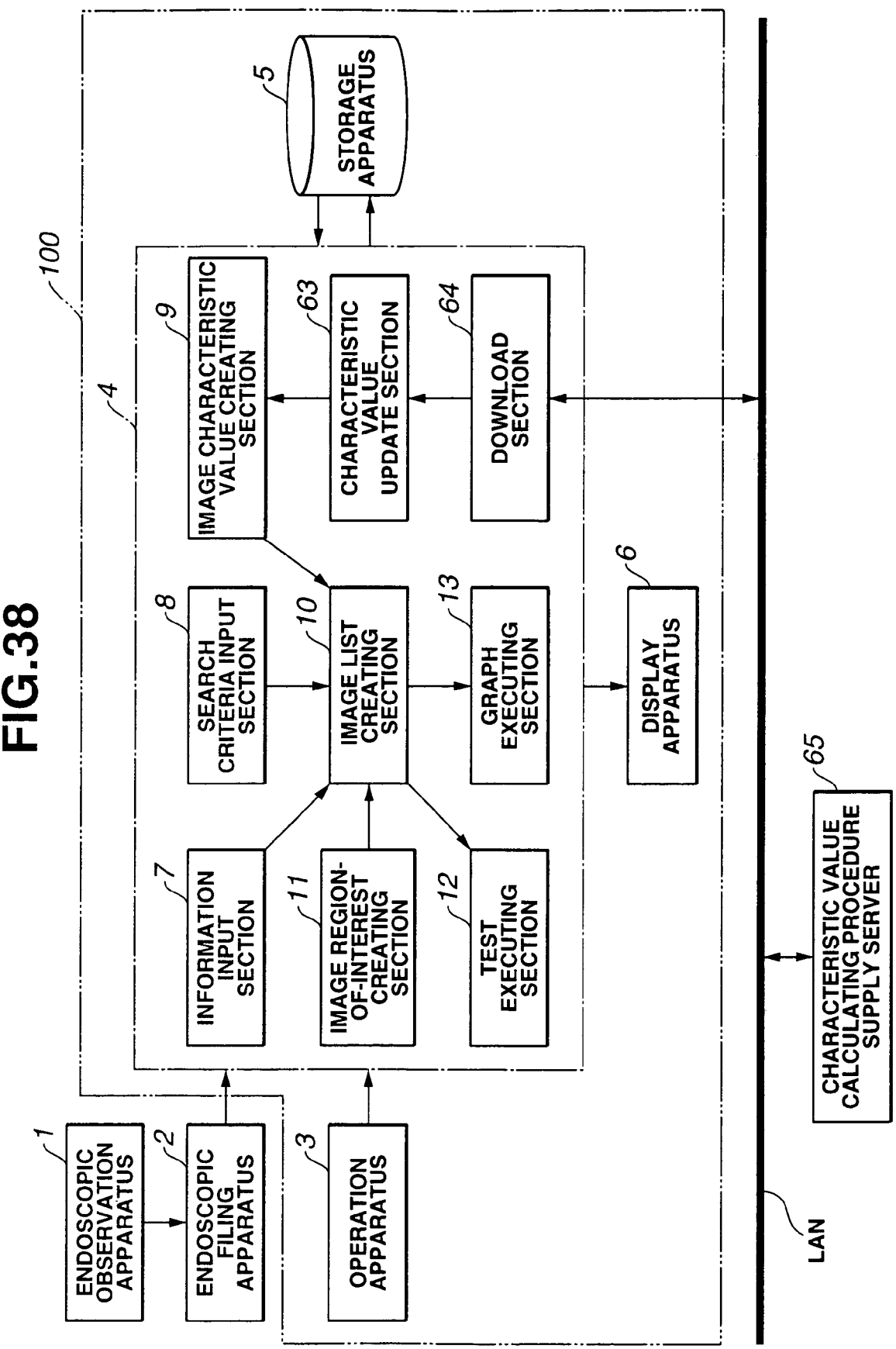
FIGS. 38 and 39 relate to a sixth embodiment of the invention.

According to this embodiment, as shown in a block diagram in FIG. 38, the computer 4 according to the first embodiment is connected to a LAN so as to perform network communication by using TCP/IP or UDP/IP as a protocol.

A characteristic value calculating procedure supply server 65 is connected to the LAN so as to perform network communication by using TCP/IP or UDP/IP as a protocol.

The characteristic value calculating procedure supply server 65 holds a characteristic value procedure archive module and returns a procedure name of a held characteristic value procedure and a version number of a characteristic value procedure archive module to an inquiry from a terminal on the network. Furthermore, the characteristic value calculating procedure supply server 65 transmits a specified characteristic value procedure archive module to a request for downloading a characteristic value procedure archive module from a terminal on the network.

A characteristic value procedure archive module includes a characteristic value procedure execution module and a diagnosis name and part name to which a characteristic value is to be applied.

The computer 4 according to the first embodiment further includes a download section 64 and a characteristic value update section 63 according to this embodiment.

The download section 64 periodically inquires of the characteristic value calculating procedure supply server 65 a procedure name of a characteristic value procedure and a version number of a characteristic value procedure archive module. The download section 64 further holds a procedure name and version number of a characteristic value procedure installed in the computer 4. The download section 64 further downloads a characteristic value procedure archive module from the characteristic value calculating procedure supply sever 65 and expands the characteristic value procedure archive module into a characteristic value procedure executable module and diagnosis and part names to which the characteristic value is to be applied. The download section 64 installs the expanded characteristic value procedure executable module into the computer 4.

The characteristic value update section 63 searches a combination of patient information, image information and region-of-interest information in the database 14 by using a diagnosis name and/or a part name as a search key. The characteristic value update section 63 transmits area data of the retrieved region-of-interest information to the image characteristic value creating section 9, calculates the characteristic value and registers the calculated characteristic value with the database 14.

(Operation)

Figure 39:
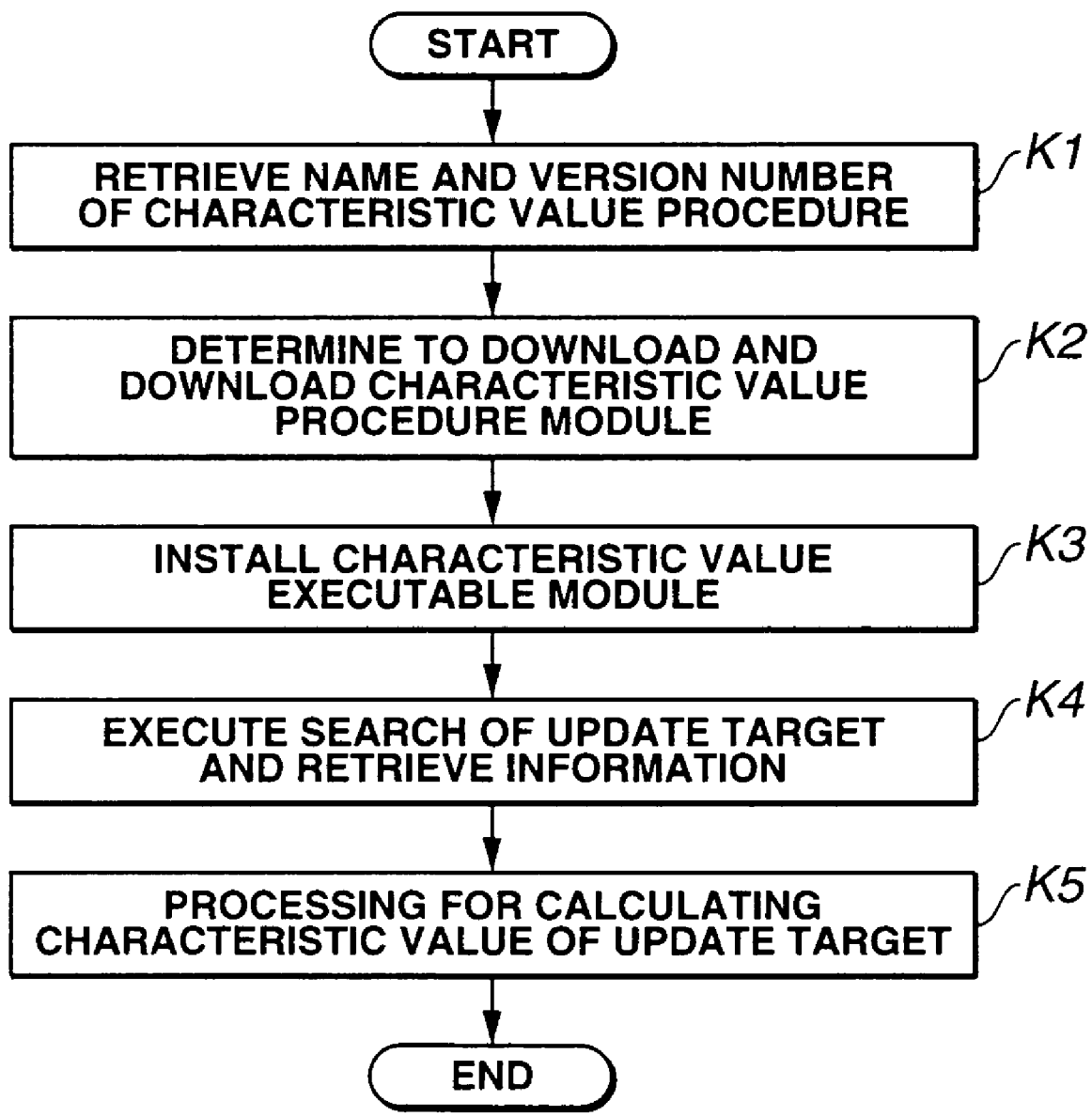

With reference to the flow diagram shown in FIG. 39, the operation will be described including downloading a characteristic value procedure from the characteristic value calculating procedure supply server 65, installing the characteristic value procedure into the computer 4 and calculating a characteristic value of a region of interest.

At a step K1, the download section 64 inquires of the characteristic value calculating procedure supply server 65 a procedure name of a held characteristic value procedure and a version number of a characteristic value procedure archive module.

Next, at a step K2, the download section 64 compares a response from the characteristic value calculating procedure supply server 65 and a procedure name and version number of a characteristic value procedure installed in the computer 4.

If the version number of a characteristic value procedure archive module held by the characteristic value calculating procedure supply server 65 is updated from the version number of a characteristic value procedure installed in the computer 4, a determination is made to download the characteristic value procedure archive module.

If a characteristic value calculating procedure having a same name as a name of a characteristic value calculating procedure held by the characteristic value calculating procedure supply server 65 is not installed in the computer 4, a determination is made to download a characteristic value procedure archive module.

The download section 64 downloads a characteristic value procedure module determined to download from the characteristic value calculating procedure supply server 65 and expands the characteristic value procedure module into a characteristic value calculating procedure executable module, a diagnosis name and a part name.

At a step K3, the download section 64 installs the characteristic value calculating procedure executable module retrieved at the step K2.

If the characteristic value procedure has been installed before the characteristic value procedure executable module is installed, the characteristic value procedure executable module is overwritten, and a corresponding processing section within the image characteristic value creating section 9 is overwritten and updated. If not installed, a new processing section is created in the image characteristic value creating section 9 to allow the selection of the connection with the characteristic value selecting section 30. Furthermore, new fields are created on the region-of-interest table in the database 14, and the data on the display column management table 41 is updated such that the fields can be listed and displayed.

At a step K4, the characteristic value updating section 63 searches a combination of the patient information table 15, image information table 16 and region-of-interest information table 17 in the database 14 by using the diagnosis name and part name retrieved at the step K2 as a search key. The search result is held in the computer 4 as an information set of patient information, image information and region-of-interest information.

At a step K5, the characteristic value updating section 63 transmits the information set held in the computer 4 at the step K4 to the image characteristic value creating section 9 and selects the name of the characteristic value procedure installed at the step K3 as a characteristic value procedure to be executed. The characteristic value selecting section 30 within the image characteristic value creating section 9 connects to the processing section for the selected characteristic value procedure, calculates a characteristic value based on image data within the image information and area data within the region-of-interest information and stores the calculation result into the field corresponding to the characteristic value procedure in the region of interest.

This processing is repeated until no characteristic value procedures to install are left.

(Advantages)

Through periodical monitor, a characteristic value calculating procedure can-be newly installed or upgraded. Furthermore, efforts of a user can be reduced by automatically searching an image to which the characteristic value calculating procedure is to be applied and applying the procedure.

Seventh Embodiment

A seventh embodiment is substantially similar to the first embodiment and only constructionally different in that the computer according to the first embodiment further includes an identifier creation executing section and an identification and categorization executing section. Here, the difference will be only described, and the same reference numerals are given to the same components, the descriptions of which will be omitted.

(Construction)

Figure 40:
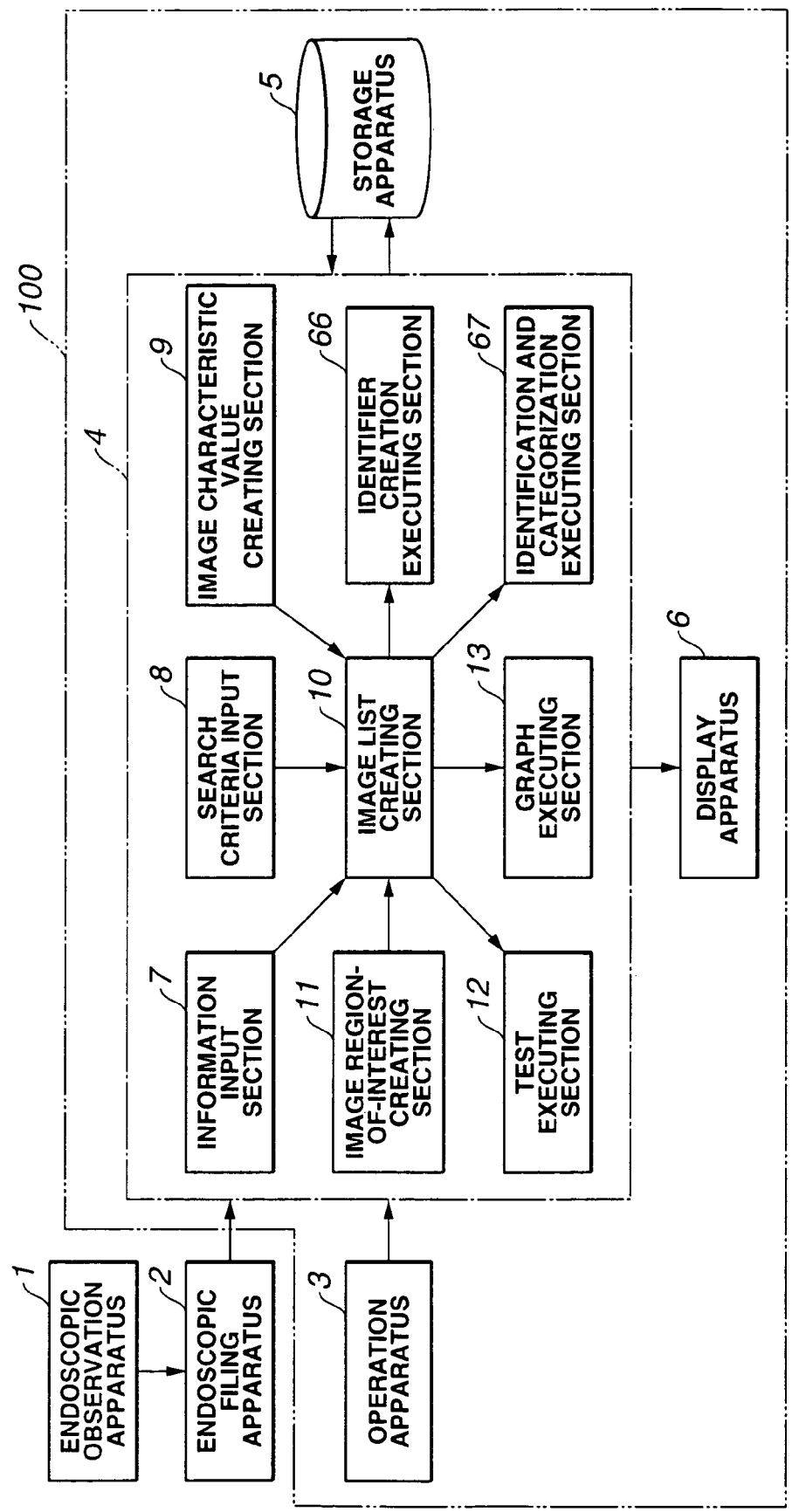

According to this embodiment, as shown in a block diagram in FIG. 40, the computer 4 according to the first embodiment further includes an identifier creation executing section 66 and an identification and categorization executing section 67.

The identification and categorization executing section 67 derives a diagnosis name on the analogy of a set of a first characteristic value and second characteristic value and the reliability relating to the analogy and outputs the diagnosis name and the reliability. The analogy of the diagnosis name and the derivation of the reliability of the analogy use an output of an identifier. According to this embodiment, a linear discriminant function is used as the identifier.

An outline of identification based on a linear discriminant function to be performed by the identification and categorization executing section 67 will be described with reference to FIG. 41.

Figure 41:
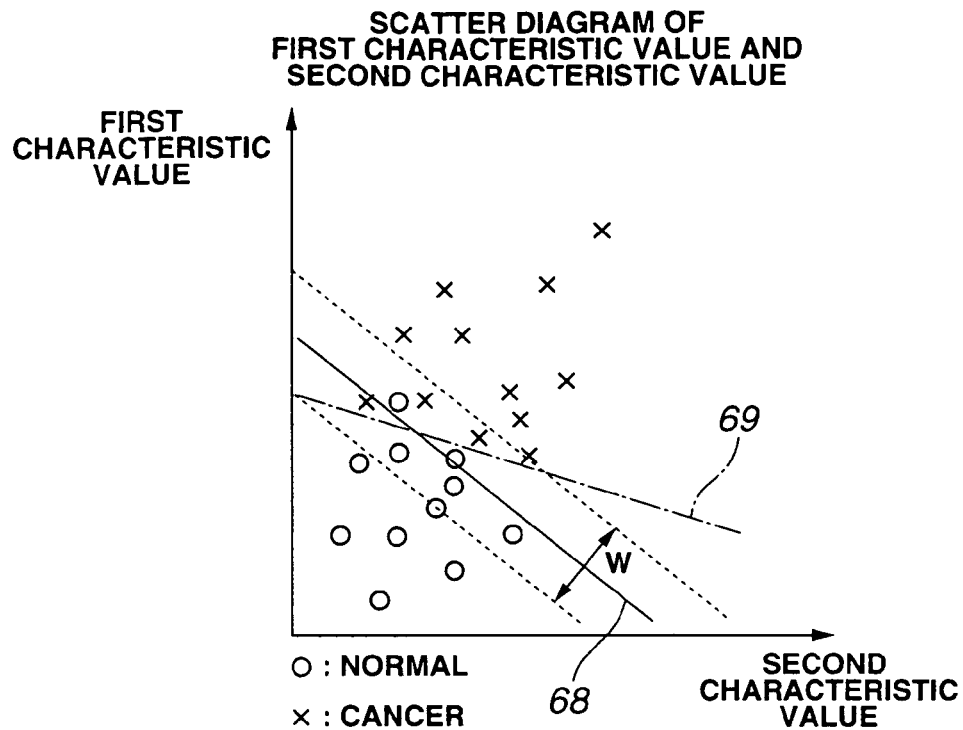

FIG. 41 shows a result from performance of conversion on an input characteristic value based on main component analysis and plot of the conversion values on a scatter diagram including a main component axis. In FIG. 41, a condition is specially established for describing identification based on a linear discriminant function. In the plot diagram, a straight line 68 representing a linear discriminant function is displayed as a solid line over other elements.

As shown in FIG. 41, distributions of plot points indicating a normal state and a cancer can be divided into upper and lower distributions with respect to the straight line 68 representing a linear discriminant function. When a plot point is above the straight line 68 representing the linear discriminant function, the identifier outputs "cancer". On the other hand, when a plot point is below the straight line 68, the identifier outputs "normal". When a plot point is in a predetermined width W with respect to the straight line 68 representing the linear discriminant function, the identifier outputs "low reliability" as the reliability. Otherwise, the identifier outputs "high reliability".

A coefficient of the linear discriminant function is stored in the storage apparatus 5, and the identification and categorization executing section 67 reads, identifies and categorizes a coefficient of the linear discriminant function from the storage apparatus 5.

In response to an external instruction for identifier creation, the identifier creation executing section 66 creates a coefficient of the linear discriminant function of the identifier. The identifier creation executing section 66 creates a coefficient of the linear discriminant function by using all data stored in the database 14 as training sample data and stores the retrieved coefficient in the storage apparatus 5.

When, in the information input section, manipulations relating to creation of an identifier are performed on image data input from the endoscopic filing apparatus 2 such as new registration with the database 14 and editing of a diagnosis name, the information input section 7 instructs the identifier creation executing section 66 to update the coefficient of the linear discriminant function of the identifier.

The information list section 10 displays the list table 37 shown in FIG. 42. A difference from the display according to the first embodiment is that the information list 40 further includes columns of a right-wrong judgement 70 and a name called diagnosis name 71 based on identification and that the menu 38 further includes an entry for execution of identification and categorization.

The column of the diagnosis name 71 based on identification displays a diagnosis name based on identification, which is output from the identification and categorization executing section 67.

As execution results from identification and categorization, the column of the right-wrong judgement 70 displays four kinds of string:

(1) O: The reliability output from the identification and categorization executing section is "high reliability" and the diagnosis name based on identification agrees with the diagnosis name;

(2) O(−): The reliability output from the identification and categorization executing section is "low reliability" and the diagnosis name based on identification agrees with the diagnosis name;

(3) X: The reliability output from the identification and categorization executing section is "high reliability" and the diagnosis name based on identification does not agree with the diagnosis name; and (4) X(−): The reliability output from the identification and categorization executing section is "low reliability" and the diagnosis name based on identification does not agree with the diagnosis name.

If right-wrong judgment results in (3) above, the information list creating section 10 highlights the corresponding row.

(Operation)

The creation of an identifier will be described. Like the operation according to the first embodiment, when a user edits a diagnosis name or image data from the endoscopic filing apparatus 2 is input to the computer 4, the information input section 7 adds or edits information in the database 14 and instructs the identifier creation executing section 66 to create an identifier.

In response to the instruction for identifier creation, the identifier creation executing section 66 creates a coefficient of a linear discriminant function by using all data stored in the database 14 as training sample data and stores the derived coefficient into the storage apparatus 5.

Next, an operation of executing identification and categorization and viewing an execution result thereof will be described.

Figure 43:
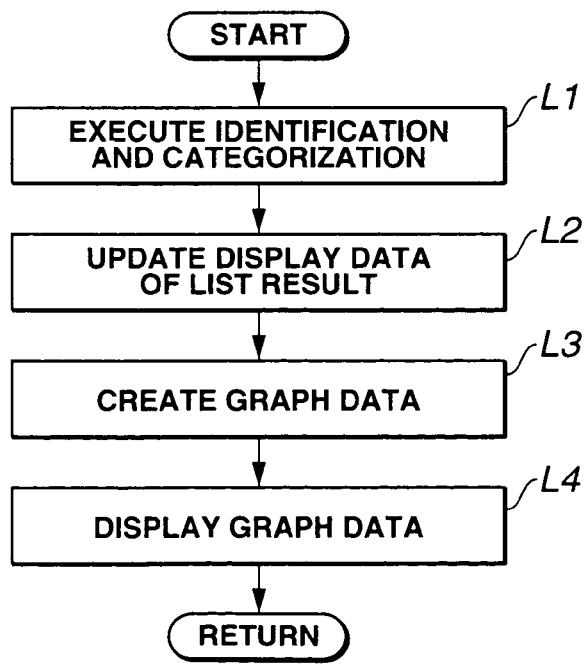

When a user selects "Execute Identification and Categorization" from the menu 38 in FIG. 42, processing advances in accordance with a flow diagram shown in FIG. 43.

At a step L1, the identification and categorization executing section 67 performs identification based on a linear discriminant function on each of all sets of patient information, image information and region-of-interest information held in the computer 4 and holds the output reliability and a diagnosis name based on the identification in association in the computer 4.

At a step L2, the list table creating section 10 updates display of the set of patient information, image information and region-of-interest information. Here, the columns of the right-wrong judgement 70 and diagnosis name 71 based on identification display data in accordance with the result in the identification and categorization executing section 67.

At a step L3, the graph executing section 13 creates a two-dimensional scatter diagram having attributes categorized based on diagnosis names from information sets of patient information, image information and region-of-interest information held at the step L1 and the reliability to be output and diagnosis name based on identification.

According to the first embodiment, a graph is created and is displayed by following the flow diagram shown in FIG. 17. At the step F1 in the flow diagram shown in FIG. 17, a graph creation condition is determined based on a selection by a user on the graph creation condition input window 33. On the other hand, according to this embodiment, at the step F1 in the flow diagram shown in FIG. 17, the identification and categorization executing section 67 selects the procedure as a two-dimensional scatter diagram, the category as a diagnosis name, the first data value and the second data value as characteristic values used for identification and categorization, and the processing advances therewith.

In this case, a graph may be created such that a straight line representing a linear discriminant function can be displayed over other elements in a two-dimensional scatter diagram.

A marker displayed in the two-dimensional scatter diagram may be highlighted in accordance with reliability, and information sets having low reliability and high reliability may be displayed with distinction therebetween.

While a two-dimensional scatter diagram is used as a graph procedure according to this embodiment, the implementation of the invention is not limited to a two-dimensional scatter diagram.

(Advantages)

An identification and categorization result can be easily checked in detail, and a load on an operator for referring to data categorized between right and wrong can be reduced.

Variation Example of Seventh Embodiment

Next, a variation example of the seventh embodiment will be described with reference to FIG. 44.

As shown in FIG. 41, a plot point having a disagreement of a diagnosis name and a diagnosis name based on identification occurs near the direct line 68 representing a linear discriminant function.

(Construction)

Accordingly, in this variation example, in order to improve the performance of an identifier, an identifier creation executing section 66 and an identification and categorization executing section 67 are provided as follows.

The identification and categorization executing section 67 uses outputs of two identifiers and infers a diagnosis name to be inferred.

A first identifier is the same identifier as the identifier according to the seventh embodiment. A second identifier is an identifier for information regarded by the first identifier as having low reliability and, like the first identifier, has a linear discriminant function represented by an alternate long and short dashed line 69 in FIG. 41. A coefficient of a second linear discriminant function is also stored in the storage apparatus 5.

The identifier creation executing section 66 creates a linear discriminant function of the first identifier and a coefficient of a linear discriminant function of the second identifier and stores the coefficients in the storage apparatus 5. The coefficient of the linear discriminant function of the first identifier is the same as that of the seventh embodiment, and all data stored in the database 14 are created as training sample data. The coefficient of the linear discriminant function of the second identifier is created by using, as training sample data, data having disagreement between a diagnosis name identified by the first identifier and a diagnosis name of image information among data stored in the database 14.

In other words, the second identifier performs identification processing on data in a range having a width W with respect to the straight line 68 representing the first linear discriminant function in FIG. 41.

(Operation)

Figure 44:
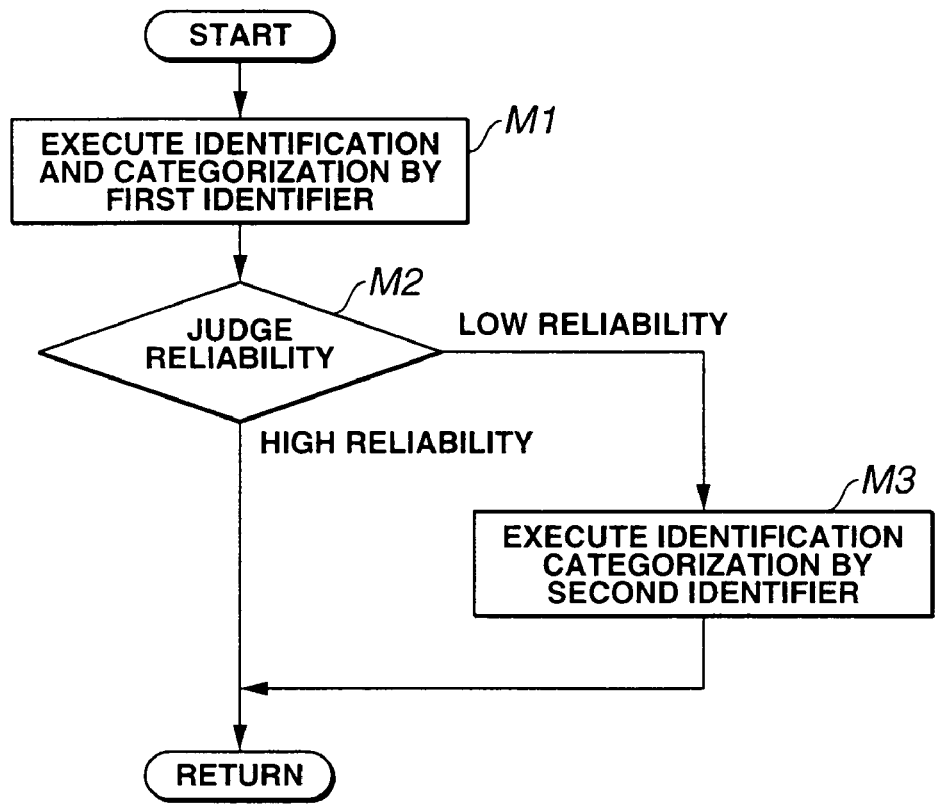

The identification and categorization executing section 67 performs identification and categorization at a step L1 in FIG. 43 by following a flow shown in FIG. 44. The other operations are similar to the operations according to the seventh embodiment.

At a step M1, the identification and categorization executing section 67 uses the first identifier to perform identification and categorization on all sets of patient information, image information and region-of-interest information held in the computer 4 and stores output reliability and diagnosis names based on identification in association in the computer 4.

At a step M2, the identification and categorization executing section 67 judges the reliability of results of identification and categorization executed at the step M1. At a step M3, the identification and categorization executing section 67 uses the second identifier to perform identification and categorization on data sets having the reliability "low" and updates the output reliability and diagnosis names based on identification held in the computer 4 so as to agree with the execution result by the second identifier. Additional processing is not performed on the data sets having the reliability "high", and subsequent steps are performed thereon.

Subsequent steps are the same as those of the seventh embodiment.

(Advantage)

The accuracy of identification and categorization can be improved.

Eighth Embodiment

An eighth embodiment is substantially similar to the seventh embodiment and is constructionally different therefrom in that a construction of a graph executing section is different from that of the seventh embodiment. The difference will be only described, and the same reference numerals are given to the same components, the descriptions of which will be omitted.

(Construction)

Figure 45:
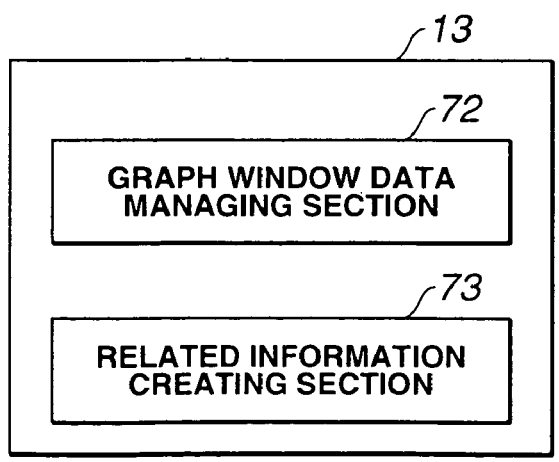
FIGS. 45 to 47 relate to an eighth embodiment of the invention.

FIG. 45 shows a block diagram of a graph executing section 13 according to this embodiment. The graph executing section 13 includes the construction the graph executing section 13 of the first embodiment and further includes a graph window data managing section 72 and a related-information creating section 73.

The graph window data managing section 72 stores, in the computer 4 for each created graph, a data set, that is, an information set having patient information, image information and region-of-interest information, which is used in the graph. When a graph is created with the execution of identification and categorization, the data set is held in connection with an identification and categorization result. Here, an identification and categorization result refers to a diagnosis name based on identification and reliability of the identification according to the seventh embodiment.

In response to a selection of a graph object on the display apparatus 6, such as a plot point in a two-dimensional scatter diagram and a bar in a histogram or bar graph, by a user on the operation apparatus 3, the graph window data managing section 72 searches and retrieves the data set corresponding to a selected graph object from data sets held in the computer 4.

When a characteristic value range is given as a search criteria, the graph window data managing section 72 searches and retrieves the data set matching with the search criteria from data sets held in the computer 4.

Figure 46:
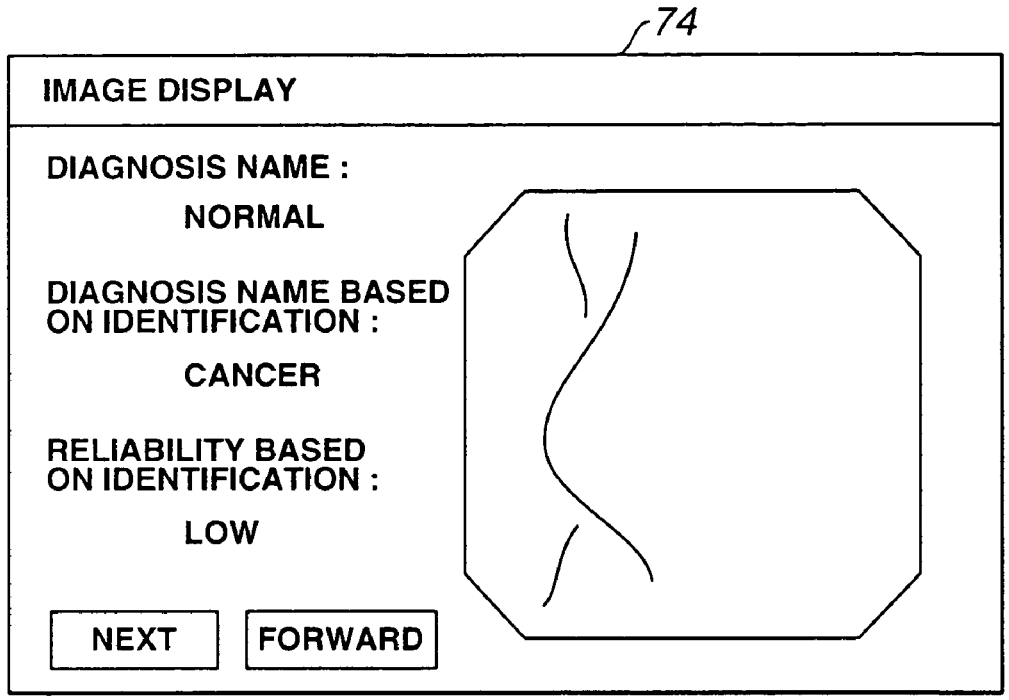

When patient information, image information, region-of-interest information and an identification and categorization result are given from the graph window data managing section 72, the related-information creating section 73 creates the display window 74 shown in FIG. 46 based on the given information and displays the created display window 74 on the display apparatus 6.

The display window 74 shown in FIG. 46 includes a Forward button 75 and a Next button 76. When a user presses the Forward button 75 or Next button 76 through the operation apparatus 3, the related-information creating section 73 newly retrieves an information'set of patient information, image information, region-of-interest information and an identification and categorization result to be displayed on the display window 74 from the graph window data management section 72. Then, the related-information creating section 73 recreates, displays and updates the display window 74.

(Operation)

Figure 47:
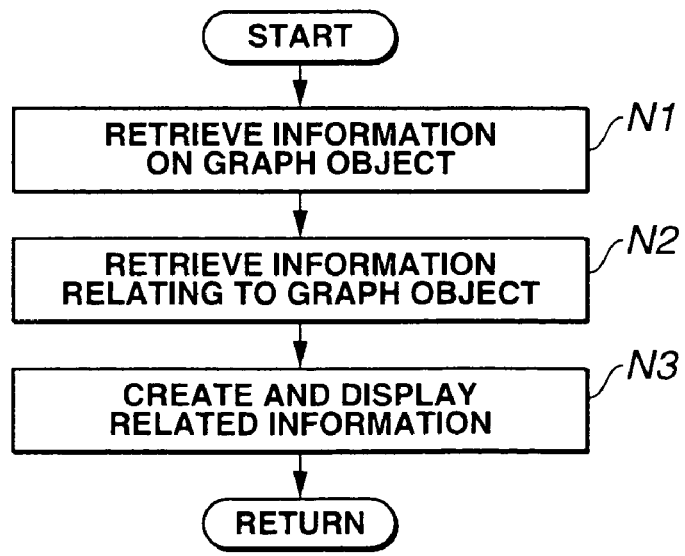

An operation by the information processor 100 to be performed when a user manipulates and/or selects, through the operation apparatus, a graph object (such as a plot point in a graph) in a graph image relating to a result of identification and categorization performed by the operation according to the seventh embodiment will be described below with reference to a flow diagram shown in FIG. 47.

At a step N1, the graph window data managing section 72 retrieves a data set of patient information, image information and region-of-interest information relating to a selected graph object and a corresponding identification and categorization result from information held in the computer 4.

At a step N2, the graph window data managing section 72 adjusts a predetermined value for a characteristic value of the region-of-interest information retrieved at the step N1 so that the graph window data managing section 72 creates a range of the characteristic value and retrieves a data set matching with the condition in the characteristic value range from data sets held in the computer 4.

At a step N3, the graph window data managing section 72 provides the related-information creating section 73 with one data set from multiple data sets (of patient information, image information, region-of-interest information, diagnosis names based on identification and reliability of identification) retrieved at the step N2. The related-information creating section 73 creates the display window 74 shown in FIG. 46 based on the given data set and displays the created display window 74 on the display apparatus 6.

When a user presses the Next button 76 on the display window 74, the related-information creating section 73 retrieves a data set before a currently displayed data set from the graph window data managing section 72 and recreates, displays and updates the display window 74.

When a user presses the Forward button 75 on the display window 74, the related-information creating section 73 retrieves a data set following a currently displayed data set from the graph window data management section 72 and recreates, displays and updates the display window 74.

(Advantages)

Information near a selected point on a graph can be easily viewed.

If a diagnosis name based on identification and categorization does not match with that of the selected graph object at the step N1, subsequent steps may be continuously performed. If the diagnosis name based on identification and categorization matches therewith, subsequent steps may be cancelled. Thus, unnecessary information may not be displayed.

As many apparently widely different embodiments of this invention may be made without departing from the spirit and scope thereof, it is to be understood that the invention is not limited to the specific embodiments thereof except as defined in the appended claims.

What is claimed is:

1. An information processor, comprising:

endoscopic image input means for inputting an endoscopic image;

information input means for inputting a category item relating to the endoscopic image;

storage means for storing the endoscopic image input by the endoscopic image input means and information input by the information input means;

search means for searching an endoscopic image from the storage means based on the category item;

characteristic value calculating means for calculating a characteristic value from the endoscopic image input by the endoscopic image input means;

calculating technique changing means for updating and/or adding a characteristic value calculating technique to be applied to the characteristic value calculating means; and detecting means for detecting a category item to be updated and/or added by the calculating technique changing means, wherein the search means searches the endoscopic image based on a detection result by the detecting means, and the characteristic value calculating means applies a characteristic value calculating means updated and/or added for the searched endoscopic image.

\* \* \* \* \*